(12) United States Patent
Hage

(10) Patent No.: US 6,526,835 B1
(45) Date of Patent: Mar. 4, 2003

(54) APPARATUS AND METHOD FOR CHARACTERIZING PHYSICAL PROPERTIES OF A TEST PIECE

(75) Inventor: Richard Todd Hage, Champlin, MN (US)

(73) Assignee: Andersen Corporation, Bayport, MN (US)

( * ) Notice: Subject to any disclaimer, the term of this patent is extended or adjusted under 35 U.S.C. 154(b) by 0 days.

(21) Appl. No.: 09/875,608

(22) Filed: Jun. 6, 2001

(51) Int. Cl.⁷ ................................................ G01B 7/16
(52) U.S. Cl. ...................................................... 73/778
(58) Field of Search ........................ 73/778, 570, 649, 73/801

(56) References Cited

U.S. PATENT DOCUMENTS

| | | | | |
|---|---|---|---|---|
| 3,984,805 A | * | 10/1976 | Silverman | 367/190 |
| 4,069,706 A | | 1/1978 | Marshall et al. | |
| 5,388,056 A | * | 2/1995 | Horiuchi et al. | 700/30 |
| 5,431,261 A | * | 7/1995 | Olgac | 188/379 |
| 5,625,145 A | * | 4/1997 | Maeno et al. | 73/501.12 |
| 5,719,324 A | * | 2/1998 | Thundat et al. | 422/88 |
| 5,737,239 A | * | 4/1998 | Horiuchi et al. | 702/33 |

OTHER PUBLICATIONS

"Standard Test Method for Dynamic Young's Modulus, Shear Modulus, and Poisson's Ratio for Advanced Ceramics by Impulse Excitation of Vibration", ASTM Designation: C 1259–96, American Society for Testing and Material (date unknown).

"Standard Test Method for Dynamic Young's Modulus, Shear Modulus, and Poisson's Ratio for Advanced Ceramics by Impulse Excitation of Vibration", ASTM Designation: C 1259–01, Reproduced by Global Engineering Documents with permission of ASTM (date unknown).

* cited by examiner

*Primary Examiner*—Max Noori
(74) *Attorney, Agent, or Firm*—Merchant & Gould P.C.

(57) ABSTRACT

An apparatus and method for non-destructively determining non-musical physical characteristics such as the Young's modulus, stiffness coefficient, and damping coefficient of a test piece of arbitrary shape. The apparatus consists of a frame having a natural vibrational frequency different from the free vibrational frequency of the test piece, a mechanism for fixing the test piece to the frame, a mechanism for initiating free vibrations in the test piece, a mechanism to measure the displacement of the test piece during the free vibrations, and a mechanism to measure time during the free vibrations. The amplitude, frequency, and decay characteristics of the free vibrations are analyzed mathematically to determine the physical characteristics. The apparatus may include a mechanism to control the initial deflection applied to the test piece. The apparatus may include a mechanism to control the initial load applied to the test piece. The apparatus may include a device such as a computer to collect, process, record, and display the information obtained.

58 Claims, 11 Drawing Sheets

APPARATUS AND METHOD FOR CHARACTERIZING PHYSICAL PROPERTIES OF A TEST PIECE

BACKGROUND OF THE INVENTION

This invention relates to an apparatus for characterizing physical properties of a test piece, and related methods.

In many circumstances, it is desirable to determine the physical properties of an object or structure. For example, in a manufacturing environment, it may be advantageous to determine selected physical properties of a product so as to verify that the product meets the minimum standards for its intended purpose. Similarly, it may be advantageous to determine the physical properties of a product in order to adjust a manufacturing process, so that a consistent and high-quality product may be produced. Furthermore, by evaluating the physical properties of a particular type of product while adjusting various process parameters, it is possible to optimize the process parameters for a particular product or process. For example, for the manufacture of a drawn polymer material, such parameters as the temperature of the molten material, the amount of draw-down, the through-put, and the viscosity of the base material may be determined and optimized through proper evaluation of physical properties of the finished product.

A wide variety of physical properties may be measured. One useful property is the elastic modulus. The elastic modulus is a ratio of the stress applied to an object or structure over strain exhibited by that object or structure.

Stress is defined as the applied force divided by the resisting area of the object. It will be appreciated that an object may be subjected to many sorts of stress, such as shear, compression, torsion, and tensile. It will also be appreciated that the resisting area of an object or structure depends on both the shape of the object and the type or direction of stress applied to it.

Strain is a relative deflection of the object in question in response to the applied stress. An object may similarly exhibit various sorts of strains depending on the stresses applied.

Regardless of the type of stress and strain, however, the elastic modulus may be understood to be an indication of an object's response to applied forces.

One particularly useful elastic modulus is the Young's modulus. The Young's modulus is a ratio of the applied tensile stress $\delta$ over the exhibited tensile strain $\epsilon$. Although a wide variety of other elastic moduli may of course be measured, it is enlightening to consider as a specific example the Young's modulus and devices known for measuring it.

Several devices are known for measuring Young's modulus. Conventional devices include destructive ("test until failure") systems and dynamic mechanical analyzers, commonly known as DMAs. Neither type of device is entirely satisfactory, however.

Conventionally, the Young's modulus of an object is determined destructively by measuring the deflection of the object while applying a gradually increasing force to the object until it "fails", that is, deforms plastically or fractures. The stress-strain relationship is then determined for the sample. The stress-strain relationship is plotted as a curve, and a straight-line fit of the curve is approximated. The slope of the line may be used as an approximation of Young's modulus.

This approach has numerous disadvantages. For example, a useful approximation of Young's modulus can only be determined if the stress-strain relationship is linear or nearly linear over a broad range. That is, the material must have a large and generally uniform range of elastic deformation. Although some materials have such properties, many others do not. In particular, many composite materials do not exhibit linear stress-strain relationships.

Also, the destruction of the object being tested is inherent in the test method. In order to obtain sufficient useful data for the straight-line fit, the sample must be tested across essentially its entire range of elastic deformation. Therefore, it is necessary to increase the applied force until the sample either deforms plastically or fractures. In either event, the sample is destroyed, and is unavailable for sale, further testing, or other purposes.

Because conventional destructive methods require a substantial range of stress-strain data to determine a useful value of Young's modulus, destructive testing is generally not suitable for determining Young's modulus at a particular stress, or for a narrow band of stresses. Conventional destructive testing typically produces only an average value for the entire range of applied stress.

In addition, destructive tests are generally limited to samples of standard size and shape. This is the case for several reasons. First, in order to calculate the stress on a sample, the resisting area of the sample must be known. Thus, in order to determine the Young's modulus of an arbitrarily-shaped product using conventional destructive methods, the geometry of the product must be carefully measured, and the area calculated. For complex shapes, this is a considerable difficulty.

Second, the Young's modulus of an object depends not only on its material and its resisting area but also on its shape. For example, a U-shaped beam generally exhibits a higher Young's modulus than a flat strip, even if the strip and the beam have the same resisting area and are made from the same material. In many cases, especially for complex shapes, it is impractical or impossible to calculate in advance the effect of a particular shape on the Young's modulus. Thus, in order to compare test subjects without performing complex corrections due to varying geometry, it is generally necessary to test a sample of standard size and shape instead of an actual product.

Although this simplification is convenient, the use of samples as opposed to actual products produces difficulties. For example, tests on samples tend to be inaccurate for orthotropic materials, that is, materials that have a directionally non-uniform structure. One common example is wood, which has a grain that is stronger in some directions than in others. Other orthotropic or partially orthotropic materials include composites, laminates, etc. Orthotropic materials pose difficulties for conventional tests for several reasons.

First, the stress and strain of orthotropic materials do not always vary linearly with increasing dimension. That is, doubling the cross-sectional area of a sample of an orthotropic material may not double the stress required to achieve a given strain, even if the material composition and shape are kept exactly the same.

Second, orientation is important for orthotropic materials. For example, an object composed of many laminated layers will have a very different Young's modulus if the layers are oriented parallel to the direction of stress than if they are perpendicular to the direction of stress. Because it may be inconvenient or impossible to produce a test sample that is representative of the orientation in which the actual product will be used, the accuracy of the test becomes questionable at best.

Dynamic Mechanical Analyzers operate according to a different principle. As previously described, the Young's modulus is a measure of material stiffness. The Young's Modulus of an object, along with the object's geometry, determine the stiffness coefficient of that object. In turn, the stiffness coefficient of an object determines the frequency at which it will vibrate. By proper analysis, it is therefore possible to determine the Young's modulus of an object if the geometry and a frequency of vibration of the object are known.

In order to obtain data, the object must of course be made to vibrate. However, the vibration must be at the free vibrational frequency for the object, also known as its natural frequency. The free vibrational frequency of an object is the frequency at which it will vibrate if it is initially disturbed but not subsequently subjected to additional forces. Such vibrations are known as free vibrations.

If an object is driven at its free vibrational frequency, also known as its harmonic frequency, the object's natural vibrations and the driving vibrations will combine additively, and the object is said to be vibrating harmonically. Harmonic vibration is generally detectable as an apparent increase in the amplitude of the object's vibrations.

DMAs exploit this natural phenomenon. Driving vibrations are applied to an object to be tested. The frequency of the vibrations is slowly adjusted until the object undergoes harmonic vibration at its free vibrational frequency. At this point the vibrations are maintained at a constant, steady-state frequency, and the driving frequency, which at this point is known to be equal to the free vibrational frequency, of the object is measured. Young's modulus is then calculated from the free vibrational frequency of the object.

However, DMAs also suffer from serious limitations.

First, as described above, the free vibrational frequency of an object depends not only on its Young's modulus but also on its geometry. As described previously with respect to destructive testing, determining the geometry of an arbitrary object may be inconvenient or impossible. Therefore, for similar reasons, DMA testing is conventionally performed on samples of standard size and shape.

However, because of this, the problems inherent in testing standard samples as opposed to actual objects, as outlined above with respect to destructive testing, also apply to DMA testing.

In addition, DMA testing is very time-consuming. In order to obtain data, the test sample must undergo steady-state harmonic vibration. Thus, DMA testing requires that the driving frequency be changed at a rate that permits the harmonic vibration to reach a steady state and be recognized. In practice, this means that the frequency of the driving vibrations must be changed very slowly. Because the range of possible natural frequencies for a test piece is quite broad, considerable time is required to perform even a single DMA test.

Also, because of the need to precisely match an initially unknown frequency for every test sample, DMA testing requires a relatively high degree of skill and training to perform reliably. The need for a highly skilled operator limits the utility of DMA testing for controlling a manufacturing line from a production floor.

Furthermore, DMA testing is severely limited in terms of the amount of data generated. The stress-strain curve of any object is never perfectly linear. That is, the Young's modulus of any object is different for different strains. For a vibration, the strain corresponds to the amplitude of the vibration. This means that the free vibrational frequency of an object varies at least slightly with the amplitude of the vibration. Because the harmonic vibrations necessary for DMA testing are steady-state, they permit measurement of only a single point of data on the stress-strain curve, and hence only a single value for Young's modulus, per test. Varying the amplitude of the vibrations to determine a value for Young's modulus at a different strain requires readjustment of the driving frequency to match the free vibrational frequency of the object for that different strain. Therefore, in order to generate a useful stress-strain curve, rather than a single approximating value, the test must be repeated many times. This can be inconvenient, especially in view of the relatively long time necessary for each individual test. In particular, the long time required renders DMA testing unsuitable for many process control applications, as it may not be possible to produce data quickly enough to permit timely adjustment of the process.

SUMMARY OF THE INVENTION

In contrast, the claimed invention is based on the observation of free vibrations in a system. Measurements of the free vibrations of the system may be used to conveniently determine physical properties of an object of an object of largely arbitrary geometry, without destroying the object being tested.

In order to appreciate the structure and function of the claimed invention, it is illustrative to consider certain properties of free vibration, and certain exemplary systems.

An object or system that is struck, deflected or otherwise disturbed and then left undisturbed undergoes free vibration. Free vibrations in an object may be represented as a single degree of freedom mass-spring-damper system 10, as illustrated in FIG. 1.

An ideal mass-spring-damper system 10 includes a mass 12, a spring 14 connecting the mass 12 to an effectively immobile base 16, and a damping element 18 also connecting the mass 12 to the base 16. In an equilibrium state, the spring 14 is neither compressed nor extended, and thus applies no net force to the mass 12. If the mass 12 is displaced by some initial distance, the spring 14 is either extended or compressed, and in either case a net force is a then applied to the mass 12. The mass 12 will then oscillate back and forth as the spring 14 alternately expands and contracts. At this point, the system 10 is undergoing free vibration.

For purposes of mathematical analysis, the physical properties of the system are defined as follows. The mass 12 has a possesses a mass M. The spring 14 has a stiffness coefficient K, also known as a spring coefficient. The damping element 16 has a damping coefficient C.

It is noted that the system illustrated in FIG. 1 is a one-dimensional system, wherein both the spring 14 and the damping element 16 are effectively massless, and wherein the mass 12 is a zero-dimensional point mass. For such a system, the entire mass M and only mass M have any effect on the system. Thus, the effective mass of the system is exactly equal to the mass of the mass 12. However, it will be appreciated by those knowledgeable in the art that for a real system in two or more dimensions, such as for example a longitudinal beam undergoing transverse longitudinal free vibrations, the mass M of a system as it relates to the following discussion would be an effective mass $M_{eff}$, rather than simply an ideal point mass. For the sake of accuracy in the following discussion, the mass of the system will be referred to as the effective mass $M_{eff}$. This matter is analyzed in greater detail below.

The stiffness coefficient K relates the force necessary to displace the mass M by a given distance, according to the equation:

$$F = Ky \qquad \text{(Equation 1)}$$

wherein

F is the force applied to the system;

K is the stiffness coefficient; and y is the displacement of the mass.

Alternatively, Equation 1 may be rearranged to solve for K:

$$K = \frac{F}{y} \qquad \text{(Equation 2)}$$

The displacement is also referred to as the deflection of the system, in particular for cases wherein the spring force is applied to bend or deflect a solid object such as a beam. It will be appreciated by those knowledgeable in the art that when an initial displacement is used to initiate free vibrations, the amplitude of the initial displacement is the same as the initial amplitude of the free vibrations.

The damping coefficient C is a measure of the forces opposing free vibrations in the system. In the simple case wherein the system is completely undamped, that is, the damping coefficient C is 0, the system vibrates according to the function:

$$\omega_n = \sqrt{\frac{K}{M_{\mathit{eff}}}} \qquad \text{(Equation 3)}$$

wherein $\omega_n$ is the natural frequency of vibrations of the system;

K is the stiffness coefficient of the spring; and $M_{\mathit{eff}}$ is the effective mass.

For an undamped system the free vibration would continue indefinitely, at an amplitude exactly equal to the original displacement, and at a frequency determined by the effective mass and the stiffness coefficient according to Equation 3.

However, in any real system, energy is lost due to various damping factors, such as friction, etc. Regardless of the precise source the damping, energy is gradually lost from any freely vibrating system. Thus, the vibrations gradually decay until the system reaches static equilibrium and the free vibrations cease altogether.

The motion of a damped system is considerably more complex than that of an undamped system. For a spring-mass-damper system as illustrated in FIG. 1, the governing equation of motion may be written:

$$M_{\mathit{eff}} \frac{d^2 y}{dt^2} + C \frac{dy}{dt} + Ky = f(t) \qquad \text{(Equation 4)}$$

wherein $M_{\mathit{eff}}$ is the effective mass;

C is the damping coefficient;

K is the stiffness coefficient; and y is the displacement of the mass.

It will be appreciated by those knowledgeable in the art that both the form of Equation 4 and the spring-mass-damper system illustrated in FIG. 1 describe linear systems, and that such systems are exemplary only. A wide variety of other damped free vibrational systems are possible, including but not limited to rotational spring-mass-damper systems. It will be further appreciated that the form of Equation 4 and the spring-mass-damper system illustrated in FIG. 1 represent one-dimensional systems, and that such systems are likewise exemplary only. Non-linear systems and systems undergoing free vibrations in two or more dimensions may be represented by equations similar to Equation 4. The mathematical analysis disclosed herein is similarly applicable to such alternative systems, and the discussion herein disclosed with respect to the exemplary system of FIG. 1 likewise applies equally to them.

Returning to the exemplary case of FIG. 1 and Equation 4, it will be appreciated that the rate at which the vibrations damp towards an amplitude of zero depends on the value of the damping coefficient C, that is, on the amount of damping present in the system. For any system, there is a quantity of damping for which the vibrations decay towards static equilibrium at the most rapid rate possible. This value of the damping coefficient is referred to as critical damping $C_c$. If the actual damping value is substantially lower than $C_c$ the actual rate at which the vibrations approach an amplitude of zero is lower than it would be if the damping were $C_c$. If the actual damping value is substantially higher than $C_c$ the system does not truly vibrate at all, but rather moves more or less steadily toward equilibrium.

A physical system may be characterized in terms of how closely the actual damping matches the critical damping value for that system. The damping ratio $\zeta$ is thus defined as $$\zeta \equiv \frac{C}{C_c} \qquad \text{(Equation 5)}$$

It will be appreciated that for a critically damped system, the damping ratio $\zeta$ is equal to 1.

It will further be appreciated that the value $C_c$ for any spring-mass-damper system must depend on the effective mass $M_{\mathit{eff}}$ and the stiffness coefficient K. In mathematical terms, this dependence follows the equation:

$$C_c = 2\sqrt{M_{\mathit{eff}} K} \qquad \text{(Equation 6)}$$

Combining Equations 5 and 6 yields the following relation:

$$\zeta = \frac{C}{2\sqrt{M_{\mathit{eff}} K}} \qquad \text{(Equation 7)}$$

Equation 7 may also be solved for the damping coefficient C as:

$$C = 2\zeta \sqrt{M_{\mathit{eff}} K} \qquad \text{(Equation 8)}$$

Returning now to the governing equation of motion as formulated in Equation 4, dividing all terms by K yields:

$$\frac{M_{\mathit{eff}}}{K} \frac{d^2 y}{dt^2} + \frac{C}{K} \frac{dy}{dt} + y = f(t) \qquad \text{(Equation 9)}$$

As may be seen, by manipulation of terms and substitution of Equations 3 and 7 the following relation may be determined:

$$\frac{C}{K} = \left(\frac{2}{2}\right)\left(\frac{C}{(\sqrt{K}\sqrt{K})}\right)\left(\frac{\sqrt{M_{eff}}}{\sqrt{M_{eff}}}\right) = \quad \text{(Equation 10)}$$

$$2\left(\frac{\sqrt{M_{eff}}}{\sqrt{K}}\right)\left(\frac{C}{2\sqrt{M_{eff}K}}\right) = \frac{2\zeta}{\omega_n}$$

In turn, substituting Equations 3 and 8 into Equation 9 yields:

$$\frac{1}{\omega_n^2}\frac{d^2y}{dt^2} + \frac{2\zeta}{\omega_n}\frac{dy}{dt} + y = f(t) \quad \text{(Equation 11)}$$

wherein $\omega_n$ is the natural frequency of the system y is the displacement of the system;

t is the time elapsed since the initiation of free vibrations; and $\zeta$ is the damping ratio of the system.

Equation 11 may be usefully solved for y in the form:

$$y = e^{(-\zeta\omega_n t)}\left(c_1\sin\left(\omega_n\sqrt{1-\zeta^2}\,t\right) + c_2\cos\left(\omega_n\sqrt{1-\zeta^2}\,t\right)\right) \quad \text{(Equation 12)}$$

wherein $c_1$ and $c_2$ are constants reflecting initial system conditions.

It is noted that $c_1$ and $c_2$ are not components of or otherwise directly related to the damping coefficient C.

It will be appreciated by those knowledgeable in the art that for physical reasons the frequency of free vibrations of a mass-spring-damper system where the damping coefficient (and hence the damping ratio) is non-zero is different from the frequency that would be observed for the same system if the damping coefficient were zero. The continuing loss of energy due to damping reduces the frequency of free vibration.

The actual frequency of free vibration for a spring-mass-damper system may be determined by inspection of Equation 12. For such an equation, the frequency is the expression associated with "t" upon which the trigonometric functions operate. Considering the case wherein the damping coefficient C and therefore the damping ratio $\zeta$ is zero, the expression $$\sqrt{1-\zeta^2}$$

equals exactly 1. Hence, Equation 12 for that special case could be written $$y = e^{(-\zeta\omega_n t)}(c_1\sin(\omega_n t) + c_2\cos(\omega_n t)) \quad \text{(Equation 13)}$$

In such a case, the frequency is $\omega_n$, as was previously stated. Similarly, in Equation 12, the frequency with a non-zero damping coefficient may be extracted as:

$$\omega_d = \omega_n\sqrt{1-\zeta^2} \quad \text{(Equation 14)}$$

wherein $\omega_d$ is the damped natural frequency of the system.

Alternately, Equation 14 may be solved in terms of $\omega_n$ as $$\omega_n = \frac{\omega_d}{\sqrt{1-\zeta^2}} \quad \text{(Equation 15)}$$

It will be appreciated that the period associated with the damped natural frequency $\omega_d$ of the system is:

$$T_d = \frac{2\pi}{\omega_d} \quad \text{(Equation 16)}$$

wherein $T_d$ is the damped natural period of the system.

Returning to Equation 12, by substitution of Equation 14 therein, it can be written as:

$$y = e^{(-\zeta\omega_n t)}(c_1\sin(\omega_d t) + c_2\cos(\omega_d t)) \quad \text{(Equation 17)}$$

Alternatively, the solution of Equation 12 may be written in a different but equivalent form:

$$y = c_3 e^{(-\zeta\omega_n t)}\sin(\omega_d t + \phi) \quad \text{(Equation 18)}$$

wherein $c_3$ is a constant reflecting initial system conditions;

$\phi$ is a phase constant reflecting initial system conditions.

It is noted that $c_3$, like $c_1$ and $c_2$, is not a component of or otherwise directly related to the damping coefficient C.

As previously noted, once free vibrations are initiated in a mass-spring-damper system, energy is gradually lost to the damper and the vibrations decay. The relative amplitude of the peaks of two vibrations may be calculated by a simple ratio of Equation 18 for two values of n. It will be appreciated that the ratio of peak values is exemplary only. Although it is convenient in certain applications to compare one peak to another, comparing waves at other phases is also mathematically possible. Such alternative wave comparisons may be equally suitable for certain applications, and may be handled similarly.

It is convenient to consider the case where the first value of n is zero, and the second remains an arbitrary value n. It will be appreciated that in such a case, t for the peak at n=0 will be 0, and t for the peak at n will be $T_d n$. Therefore:

$$\frac{y_0}{y_{0+n}} = \quad \text{(Equation 19)}$$

$$\frac{c_3 e^{(-\zeta\omega_n t)}\sin(\omega_d 0 + \phi)}{c_3 e^{(-\zeta\omega_n t + T_d n)}\sin(\omega_d T_d n + \phi)} = \frac{e^{-\zeta\omega_n t}}{e^{-\zeta\omega_n t + T_d n}} = e^{\zeta\omega_n T_d n}$$

Taking the natural log of both sides yields the expression:

$$l\left(\frac{y_0}{y_{0+n}}\right) = l e^{\zeta\omega_n T_d n} = \zeta\omega_n T_d n \quad \text{(Equation 20)}$$

Equation 20 can be solved in terms of $\zeta$ as:

$$\zeta = \frac{l\left(\frac{y_0}{y_{0+n}}\right)}{\omega_n T_d n} \quad \text{(Equation 21)}$$

With substitution from Equations 14 and 16, Equation 21 may in turn be expressed as:

$$\zeta = \frac{l\left(\frac{y_0}{y_{0+n}}\right)}{\omega_n T_d n} = \frac{l\left(\frac{y_0}{y_{0+n}}\right)}{\omega_n\left(\frac{2\pi}{\omega_d}\right)n} = \frac{l\left(\frac{y_0}{y_{0+n}}\right)}{\omega_n\left(\frac{2\pi}{\omega_n\sqrt{1-\zeta^2}}\right)n} = \sqrt{1-\zeta^2}\frac{l\left(\frac{y_0}{y_{0+n}}\right)}{2\pi n}$$ (Equation 22)

Equation 22 represents an exact and general solution for any value of the damping ratio $\omega$. However, in practice, many systems of interest have a damping ratio $\omega$ that is substantially less than 1: It will be appreciated by those knowledgeable in the art that if the damping ratio $\omega$ substantially less than 1, the value of the expression $$\sqrt{1-\zeta^2}$$

closely approximates 1.

Using this approximation, Equation 22 may be simplified to the form:

$$\zeta = \frac{l\left(\frac{y_0}{y_{0+n}}\right)}{2\pi n}$$ (Equation 23)

Based on the above mathematical derivations, it is possible to modify and substitute various of the preceding equations into Equation 6 such that the damping coefficient C is expressed in terms of directly measurable variables. First, Equation 3 is substituted into Equation 8:

$$C = 2\zeta\sqrt{M_{eff}K} = 2\zeta M\sqrt{\frac{K}{M_{eff}}} = 2\zeta M_{eff}\omega_n$$ (Equation 24)

Then Equation 24 is rearranged into equivalent forms:

$$C = 2\zeta M_{eff}\omega_n = \frac{2\zeta M_{eff}}{\frac{1}{\omega_n}} = \frac{4\pi\zeta M_{eff}}{\frac{2\pi}{\omega_n}} =$$ (Equation 25)

$$\left(\frac{4\pi M_{eff}}{\left(\frac{2\pi}{\omega_n}\right)}\right)\frac{1}{\sqrt{1-\zeta^2}}\zeta = \left(\frac{4\pi M_{eff}}{\left(\frac{2\pi}{\omega_n\sqrt{1-\zeta^2}}\right)}\right)\left(\frac{\zeta}{\sqrt{1-\zeta^2}}\right)$$

Next, Equation 14 is substituted into Equation 25:

$$C = \left(\frac{4\pi M_{eff}}{\left(\frac{2\pi}{\omega_n\sqrt{1-\zeta^2}}\right)}\right)\left(\frac{\zeta}{\sqrt{1-\zeta^2}}\right) = \left(\frac{4\pi M_{eff}}{\left(\frac{2\pi}{\omega_n}\right)}\right)\left(\frac{\zeta}{\sqrt{1-\zeta^2}}\right)$$ (Equation 26)

Then, Equation 16 is substituted into Equation 26:

$$C = \left(\frac{4\pi M_{eff}}{\left(\frac{2\pi}{\omega_n}\right)}\right)\left(\frac{\zeta}{\sqrt{1-\zeta^2}}\right) = \frac{4\pi M_{eff}}{T_d}\left(\frac{\zeta}{\sqrt{1-\zeta^2}}\right)$$ (Equation 27)

Finally, Equation 23 is substituted into Equation 28:

$$C = \frac{4\pi M_{eff}}{T_d}\left(\frac{\zeta}{\sqrt{1-\zeta^2}}\right) = \left(\frac{4\pi M_{eff}}{T_d}\right)\left(\frac{\ln\left(\frac{y_0}{y_{0+n}}\right)}{2\pi n\sqrt{1-\left(\frac{\ln\left(\frac{y_0}{y_{0+n}}\right)}{2\pi n}\right)^2}}\right)$$ (Equation 29)

C is the damping coefficient;
$M_{eff}$ is the effective mass;
$T_d$ is the damped natural period of the system;
$Y_0$ is the peak displacement of the system after zero free vibrations;
n is the number of free vibrations; and
$y_{0+n}$ is the peak displacement of the system after n free vibrations.

It is similarly possible to calculate a value of the stiffness coefficient K for a system undergoing free vibrations without depending on the geometry of the system. Returning to Equation 3, and solving it in terms of K yields the relation:

$$K = \omega_n^2 M$$ (Equation 30)

wherein
K is the stiffness coefficient of the spring
$\omega_n^2$ is the natural frequency of vibrations; and
$M_{eff}$ is the effective mass.

Substitution of the expression for $\omega_n$ from Equation 15 results in the relation:

$$K = \left(\frac{\omega_d}{\sqrt{1-\zeta^2}}\right)^2 M_{eff} = \frac{\omega_d^2 M_{eff}}{1-\zeta^2}$$ (Equation 31)

Equation 16 may be rearranged to solve for the damped natural frequency $\omega_d$:

$$\omega_d = \frac{2\pi}{T_d}$$ (Equation 32)

Substituting Equation 32 into Equation 31 results in the relation:

$$K = \frac{\left(\frac{2\pi}{T_d}\right)^2 M_{eff}}{1-\zeta^2} = \frac{4\pi^2 M_{eff}}{T_d^2(1-\zeta^2)}$$ (Equation 33)

Substitution of the expression for $\zeta$ from Equation 22 yields:

$$K = \frac{4\pi^2 M_{eff}}{T_d^2\left(1-\left(\frac{l\left(\frac{y_0}{y_{0+n}}\right)}{2\pi n}\right)^2\right)}$$ (Equation 34)

wherein
K is the stiffness coefficient;
$M_{eff}$ is the effective mass;
$T_d$ is the damped natural period of the system;
$Y_0$ is the peak displacement of the system after zero free vibrations;

$Y_{0+n}$ is the peak displacement of the system after n free vibrations; and n is the number of free vibrations.

As was pointed out with respect to Equation 1, the force necessary to displace any spring-mass-damper system is a function of the stiffness coefficient and the displacement. In addition, in many useful cases, the force necessary to displace or deflect a system of a particular type is known or may be calculated based on the structure of that system.

It is useful to consider the exemplary case of a spring-mass-damper system having a beam undergoing a transverse longitudinal deflection. Two exemplary systems of this type may be seen in FIGS. 2–5.

It will be appreciated by those knowledgeable in the art that for a beam system as described above, the force necessary to cause a deflection at a particular point along the length of the beam depends in part on the location of the point or points at which the beam is secured, and likewise on the location of the point for which the deflection of the beam is to be established. FIG. 2 illustrates an exemplary system 20 having a longitudinal beam 22, fixed at a first end 24. The beam 22 has a center of mass 26. FIG. 3 illustrates the beam 22 with a second end 28 displaced. The force that must be applied to the second end 28 to establish a deflection of the beam 22 at the second end 28 may be determined according to the relation:

$$F = \frac{3EI}{L^3} y \qquad \text{(Equation 35)}$$

wherein

F is the applied force;

E is the elastic modulus or Young's modulus of the beam

I is moment of inertia of the beam;

L is the distance between the fixed point and the point at which deflection is determined; and y is the distance of the beam's deflection at the second end.

It will be appreciated by those knowledgeable in the art that for a beam system as illustrated in FIGS. 2 and 3, L is equal to the length of the beam. That is, the first end 24 is fixed, and the second end 28 is deflected, so that the L is the distance between them, the full length of the beam. Such a configuration is convenient for certain applications. However, it will be appreciated that this configuration is exemplary only, and that the displacement may be measured at essentially any point along the length of the beam. Consequently, L is not necessarily equal to the length of the beam for all suitable systems.

FIG. 4 illustrates a system 30 including a longitudinal beam 32, fixed at a first end 34 and at a second end 38. The beam has a center of mass 36. FIG. 5 illustrates the beam 32 with the center of mass 36 of the beam 32 displaced. The force that must be applied to the center of mass 36 to establish a deflection at the center of mass 36 may be determined according to the relation:

$$F = \frac{192EI}{L^3} y \qquad \text{(Equation 36)}$$

wherein y is the distance of the beam's deflection at the center of mass.

As noted previously, L is not necessarily equal to the length of the beam for all suitable systems. For a system wherein there are two or more fixed points, L is determined from the distance to the nearest fixed point. It will be appreciated by those knowledgeable in the art that for a beam system as illustrated in FIGS. 4 and 5, L is equal to half the length of the beam.

The values 3 and 192 in Equations 35 and 36 are geometric coefficients that correspond to the arrangement of the beam within the system. It will be appreciated by those knowledgeable in the art that the choice of a point on the beam at which to establish the displacement of the beam may be essentially arbitrary. The end points and the center of mass are often used as a matter of convenience, but other locations on the beam may be equally suitable. For other locations or for other systems based on a longitudinal beam, coefficients other than those in Equations 35 and 36 are applicable. In general, for a longitudinal beam, the equation of force will be of the form:

$$F = \frac{k'' EI}{L^3} y \qquad \text{(Equation 37)}$$

wherein k" is a geometric coefficient corresponding to the arrangement of the beam. It is noted that although k" is dependent on the arrangement of the beam as a whole within the test system, k" is not dependent on the internal geometry of the beam.

In physical terms, the value of k" depends on the amount of deflection that is enabled for a given system at a given force. It will be appreciated by those knowledgeable in the art that a beam fixed at both ends requires substantially more force to deflect than a beam that is fixed at one end. The differing values of k" reflect this physical difference.

It will be appreciated by those knowledgeable in the art that the choice of a point on the beam at which to establish the displacement of the beam may be essentially arbitrary. The end points and the center of mass are often used as a matter of convenience, but other locations on the beam may be equally suitable.

It is also noted that k" is not a component of or otherwise directly related to the stiffness coefficient K.

Methods for calculating the applicable coefficient k" are well known, and are not described further herein. Similarly, methods for calculating the necessary force in general for a given displacement in systems other than beams is also well-known, and are not described further herein.

The moment of inertia I of any structure is dependent on the distribution of mass and on the geometry of the point about which the object is to be moved. It will be appreciated by those knowledgeable in the art that the internal structure is relevant to the moment of inertia only in so far as it affects the mass distribution. Thus, so long as the density is constant with respect to the motion, the internal structure of the system has no direct effect on the moment of inertia.

For example, for a beam as in FIGS. 2–5, so long as the distribution of mass of the beam is constant along the beam's length, it is not necessary to know the cross-sectional structure of the beam. A solid cylindrical beam and a hollow square beam of equal length and equal mass per unit length have exactly the same moment of inertia about their end points. Thus, for beams of constant linear density, the internal structure need not even be determined in order to calculate the moment of inertia.

Combination of Equations 1 and 37 yields the following relation:

$$Ky = \frac{k''EI}{L^3} y \qquad \text{(Equation 38)}$$

Dividing both sides of Equation 38 by y and solving for E results in:

$$E = \frac{KL^3}{k''I} \qquad \text{(Equation 39)}$$

Substituting the expression for K from Equation 34 into Equation 39 gives:

$$E = \frac{\left(\frac{4\pi^2 M_{eff}}{T_d^2 \left(1 - \frac{l\left(\frac{y_0}{y_{0+n}}\right)}{2\pi n}\right)^2}\right) L^3}{k''I} \qquad \text{(Equation 40)}$$

Equation 40 may be simplified into the form:

$$E = \frac{4\pi^2 M_{eff} L^3}{k'' T_d^2 I \left(1 - \frac{l\left(\frac{y_0}{y_{0+n}}\right)}{2\pi n}\right)^2} \qquad \text{(Equation 41)}$$

wherein

E is the Young's modulus of the beam;

L is the distance between the fixed point and the point at which deflection is determined;

k" is a geometric coefficient corresponding to the arrangement of the beam;

$M_{eff}$ is the effective mass;

$T_d$ is the damped natural period of the system;

I is moment of inertia of the beam;

$y_0$ is the peak displacement of the system after zero free vibrations;

$Y_{0+n}$ is the peak displacement of the system after n free vibrations; and n is the number of free vibrations.

As previously noted, for a real system as opposed to a zero-dimensional ideal mass-damper-system, the effective mass $M_{eff}$ will not necessarily be equal to the simple total mass of the system. For a beam system fixed at one end and deflected at the other end as illustrated in FIGS. 2 and 3, the effective mass $M_{eff}$ may be described according to the relation:

$$M_{eff} = 0.2357 M_{test} \qquad \text{(Equation 42)}$$

wherein $M_{test}$ is the measured mass of the beam.

Similarly, for a beam system fixed at both ends and deflected at the center of mass as illustrated in FIGS. 4 and 5, the effective mass $M_{eff}$ may be described according to the relation:

$$M_{eff} = 0.3610 M_{test} \qquad \text{(Equation 43)}$$

The values 0.2357 and 0.3610 in Equations 42 and 43 are geometric coefficients that correspond to the relative amount of motion of the beam along its length, which depends in turn on the relative location of the fixing point or points along the length of the beam. In general, for a longitudinal beam, the effective mass will be of the form:

$$M_{eff} = k' M_{test} \qquad \text{(Equation 44)}$$

wherein k' is a geometric coefficient corresponding to the location along the length of the beam of the point at which force is applied.

In physical terms, the value of k' depends on the aggregate deflection of the beam when force is applied at a given point. It will be appreciated by those knowledgeable in the art that when a beam that is fixed at a point or points is deflected, the fixed points of the beam do not deflect at all. Thus, a deflection of amplitude y at any particular point on the beam does not imply that the entire beam has moved a distance y. This variation in the deflection of various parts of the beam may be accounted for by use of the coefficient k'. In effect, k' changes the effective mass of the beam. Although physically the mass of the beam is constant while the relative displacement during free vibration varies with position along the length of the beam, it is mathematically convenient and functionally equivalent to treat the system as though the displacement of the beam is uniform along its length while effectively altering the mass of the beam.

The relative motion of the system as a whole depends in part on the number and location of the fixed points. This physical difference is reflected accounted for with differing values of k'.

It is noted that k' is not a component of or otherwise directly related to the stiffness coefficient K.

Methods for calculating the value of the coefficient k' are well known, and are not described further herein.

It will be appreciated by those knowledgeable in the art that 0.2357 and 0.3610, the exemplary values of k' in Equations 42 and 43, are approximations. However, the value of k' may be calculated to any arbitrary precision.

It will also be appreciated by those knowledgeable in the art that as a practical matter, when observing an actual spring-mass-damper system, it may be convenient to attach a sensor to the system in order to facilitate measurement of the displacement during free vibration. For example, in the case of the beam systems shown in FIGS. 2–5, it may be convenient to attach a sensor to the beam. It will be appreciated that the additional mass of a sensor will change the effective mass of the system. This may be accounted for by adding a term to Equation 44:

$$M_{eff} = k M_{sensor} + k' M_{test} \qquad \text{(Equation 45)}$$

wherein k is a geometric coefficient corresponding to the location of the sensor's center of mass along the length of the beam; and $M_{sensor}$ is the mass of the sensor.

It will be appreciated that a sensor placed at a fixed point of a system would not contribute any effective mass to the system, since it would not move. In such a case, the value of k would be 0. Contrariwise, a sensor placed at the point at which displacement is a maximum would contribute its entire mass to the system as effective mass. In such a case, the value of k would be 1.

Although the actual mass of a sensor does not depend on its location, the system may be treated and analyzed as though this were the case by the use of the coefficient k to adjust the contribution of the sensor to the system's total effective mass.

It is noted that k is not a component of or otherwise directly related to the stiffness coefficient K.

It will be appreciated by those knowledgeable in the art that for certain systems, including but not limited to the beam systems illustrated in FIGS. 2–5, it is convenient to locate the sensor such that k has a value of 1. For a beam system fixed at one end as illustrated in FIGS. 2–3, the sensor would be located at the second end 28. For a beam system fixed at both ends as illustrated in FIGS. 4-5, the sensor would be located at the beam's center of mass 36. However, although such arrangements may be convenient for certain applications, it will be appreciated that they are exemplary only, and that the sensor could be placed in other locations. The value of k may be calculated for any arbitrary location of the sensor's center of mass.

Methods for calculating the value of the coefficient k are well known, and are not described further herein.

Substitution of Equation 45 into Equations 29, 34, and 41 yields the following relations:

$$C = \left( \frac{4\pi(kM_{sensor} + k'M_{test})}{T_d} \right) \frac{\ln\left(\frac{y_0}{y_{0+n}}\right)}{\sqrt{1 - \left(\frac{\ln\left(\frac{y_0}{y_{0+n}}\right)}{2\pi n}\right)^2}}$$ (Equation 46)

wherein

C is the damping coefficient;

k is a geometric coefficient corresponding to sensor location;

$M_{sensor}$ is the mass of the sensor;

k' is a geometric coefficient corresponding to the location along the length of the beam of the point at which force is applied;

$M_{test}$ is the mass of the beam;

$T_d$ is the damped natural period of the system;

$y_0$ is the peak displacement of the system after zero free vibrations;

n is the number of free vibrations; and $Y_{0+n}$ is the peak displacement of the system after n free vibrations.

$$K = \frac{4\pi^2(kM_{sensor} + k'M_{test})}{T_d^2\left(1 - \left(\frac{\ln\left(\frac{y_0}{y_{(0+n)}}\right)}{2\pi n}\right)^2\right)}$$ (Equation 47)

K is the stiffness coefficient;

k is a geometric coefficient corresponding to sensor location;

$M_{sensor}$ is the mass of the sensor;

k' is a geometric coefficient corresponding to the location along the length of the beam of the point at which force is applied;

$M_{test}$ is the mass of the beam;

$T_d$ is the damped natural period of the system;

$y_0$ is the peak displacement of the system after zero free vibrations;

$y_{0+n}$ is the peak displacement of the system after n free vibrations; and n is the number of free vibrations.

$$E = \frac{4\pi^2 L^3(kM_{sensor} + k'M_{test})}{k''T_d^2 I\left(1 - \left(\frac{\ln\left(\frac{y_0}{y_{(0+n)}}\right)}{2\pi n}\right)^2\right)}$$ (Equation 48)

E is the Young's modulus of the beam;

L is the distance between the fixed point and the point at which deflection is determined;

k is a geometric coefficient corresponding to sensor location;

$M_{sensor}$ is the mass of the sensor;

k' is a geometric coefficient corresponding to the location along the length of the beam of the point at which force is applied;

$M_{test}$ is the mass of the beam;

k" is a geometric coefficient corresponding to the arrangement of the beam;

$T_d$ is the damped natural period of the system;

I is moment of inertia of the beam;

$y_0$ is the peak displacement of the system after zero free vibrations;

$y_{0+n}$ is the peak displacement of the system after n free vibrations; and n is the number of free vibrations.

It will be appreciated by those knowledgeable in the art that although the beam systems illustrated in FIGS. 2–5 are analyzed mathematically herein, they are exemplary only. A wide variety of other systems exhibiting free vibrations may be equally suitable.

For example, for certain applications it may be advantageous to initiate transverse longitudinal free vibrations in a beam fixed at its center of mass. Such a system is illustrated in FIGS. 10 and 11. FIG. 10 illustrates an exemplary system 50 having a longitudinal beam 52, fixed at its center of mass 56. The first and second ends 54 and 58 are free to move. FIG. 11 illustrates the beam 52 with the first and second ends 54 and 58 displaced.

Such a system may be analyzed mathematically in a fashion similar to that disclosed herein with respect to the systems illustrated in FIGS. 2–5. However, for the sake of brevity, the system of FIGS. 10 and 11 is not analyzed mathematically herein. Similarly, systems with test pieces other than longitudinal beams are not analyzed mathematically herein. However, it will be appreciated that in addition to those systems specifically analyzed herein, other systems utilizing longitudinal beams as well as systems utilizing test pieces with configurations other than longitudinal beams may be equally suitable.

It will be appreciated by those knowledgeable in the art that for a real system, as opposed to the one-dimensional ideal system illustrated in FIG. 1, free vibration is possible in multiple directions and orientations, or modes. With regard to multiple modes of free vibration, it is again illustrative to consider the exemplary beam system of FIGS. 2 and 3.

As previously described, FIGS. 2 and 3 illustrate an exemplary system 20 including a beam 22 fixed at a first end. FIG. 2 illustrates the beam 22 in an undeflected or neutral position. FIG. 3 illustrates the beam 22 with a transverse longitudinal deflection, as would be observed during transverse longitudinal free vibration.

FIGS. 6 and 7 illustrate the same system 20 from the perspective of the second end 28. FIG. 6 illustrates the beam 22 in a neutral position. FIG. 7 illustrates the beam 22 with a torsional deflection, as would be observed during torsional free vibration. As shown, the second end 28 of the beam 22 is twisting about an axis 40 running longitudinally through the beam 22.

It will be appreciated by those knowledgeable in the art that the vibratory modes illustrated in FIGS. 2, 3, 6 and 7 are exemplary only, and that additional vibratory modes beyond transverse longitudinal and torsional, including but not limited to compressional, are possible. In addition, although the vibratory modes illustrated in FIGS. 2, 3, 6, and 7 are shown individually for purposes of clarity, it will be appreciated that it is possible for a single system to vibrate simultaneously in multiple modes.

It will also be appreciated that, although the longitudinal beam illustrated in FIGS. 2, 3, 6, and 7 has a simple rectangular cross-section, this configuration is exemplary only. The principles of the claimed invention are equally applicable to beams of essentially arbitrary cross-section, and to objects other than longitudinal beams, as is elsewhere noted herein.

It will further be appreciated that a given system will not necessarily have the same free vibrational properties in all vibratory modes.

For example, it will be appreciated by those knowledgeable in the art that the effective mass of a system will not necessarily be the same for different vibratory modes. This is because the relative amount of motion of different parts of the system varies with the mode of vibration. For example, referring again to FIGS. 2, 3, 6, and 7 it will be appreciated that the effective mass of the beam 42 for the transverse longitudinal free vibrations illustrated in FIGS. 2 and 3 will not necessarily be the same as the effective mass of the beam 42 for the torsional free vibrations illustrated in FIGS. 6 and 7.

Similarly, the damping coefficient, stiffness coefficient, and Young's modulus of a given system will not necessarily be equal for different modes of vibration.

For a real system, therefore, Equations 29, 34, and 41 provide values of C, K, and E that are particular to a single mode of vibration. For example, for a beam system as those illustrated in FIGS. 2–5, the mode of vibration under consideration is transverse longitudinal vibration. Thus, Equations 29, 34, and 41 may be more specifically written as $$C_L = \left(\frac{4\pi(kM_{sensor} + k'M_{test})}{T_d}\right) \frac{\ln\left(\frac{y_0}{y_{(0+n)}}\right)}{2\pi n} \sqrt{1 - \left(\frac{\ln\left(\frac{y_0}{y_{(0+n)}}\right)}{2\pi n}\right)^2}$$ (Equation 49)

wherein $C_L$ is the transverse longitudinal damping coefficient.

$$K_L = \frac{4\pi^2(kM_{sensor} + k'M_{test})}{T_d^2\left(1 - \left(\frac{\ln\left(\frac{y_0}{y_{(0+n)}}\right)}{2\pi n}\right)^2\right)}$$ (Equation 50)

$K_L$ is the transverse longitudinal stiffness coefficient.

$$E_L = \frac{4\pi^2 L^3(kM_{sensor} + k'M_{test})}{k''T_d^2 I\left(1 - \left(\frac{\ln\left(\frac{y_0}{y_{(0+n)}}\right)}{2\pi n}\right)^2\right)}$$ (Equation 51)

$E_L$ is the transverse longitudinal Young's modulus of the beam;

It will be appreciated by those knowledgeable in the art that the values of k, k', k", $T_d$, and I will also be particular to each mode of vibration of the system. For example, for the transverse longitudinal vibration of the systems illustrated in FIGS. 2–5 these factors could be identified as $k_L$, $k'_L$, $k''_L$, $T_{dL}$, and $I_L$. However, to avoid unnecessarily complicating the notation, when solving for E, C, or K in a particular mode of vibration, the factors k, k', k", $T_d$, and I are assumed herein to be the appropriate factors for that mode.

It is noted that Equation 49 permits calculation of the damping coefficient from a mass, a measured period, and two measured peak displacements. In particular, it is noted that Equation 49 does not depend on the shape or geometry of the test piece.

Likewise, it is noted that Equation 50 permits calculation of the stiffness coefficient from a measured mass, a measured period, and two measured peak displacements. In particular, it is noted that Equation 50 does not depend on the shape or geometry of the test piece.

It is noted that Equation 51 permits calculation of the stiffness coefficient from a measured mass, a measured period, a measured length, and two measured peak displacements. However, Equation 51 does not depend on the shape or geometry of the beam, so long as the density of the beam is constant along its length.

In view of the preceding, it is the purpose of the claimed invention to overcome the deficiencies of existing apparatuses and methods for determining non-musical physical properties of objects.

According to the principles of the claimed invention, free vibrations are initiated in a test piece and are observed as they decay in amplitude, without continued driving. Data from the free vibrations as they decay is then analyzed to determine one or more physical properties of the test piece. Testing according to the principles of the claimed invention therefore provides data regarding physical properties across a large dynamic range with only a single test. Testing is quick, simple, and non-destructive to the test piece. Furthermore, a sample of arbitrary geometry may be tested without a need for complex geometric analysis. Because of this, it is possible to test a piece of an actual product rather than a standard sample, and the inaccuracies inherent in testing samples are avoided.

It is also the purpose of the claimed invention to provide an apparatus for measuring at least one non-musical physical property of a test piece.

An embodiment of a test apparatus in accordance with the principles of the claimed invention includes a frame with a natural vibrational frequency that is different from the anticipated free vibrational frequency of the test piece. It also includes fixing means for fixing the test piece to the apparatus at at least one fixing point, so that the test piece may undergo free vibrations. The apparatus also includes initiating means to initiate vibrations within the test piece. The apparatus further includes displacement measuring means to measure the displacement of the test piece and time measuring means in communication with the displacement measuring means so as to measure the time-varying displacement of the test piece as it undergoes free vibration.

Another embodiment of a test apparatus in accordance with the principles of the claimed invention includes a mechanism for collecting measurements of displacement and time. The collecting mechanism may include a computer.

Another embodiment of a test apparatus in accordance with the principles of the claimed invention includes a mechanism for processing measurements of displacement and time so as to determine the physical properties of the test piece. The processing mechanism may include a computer.

Another embodiment of a test apparatus in accordance with the principles of the claimed invention includes a mechanism for recording measurements of displacement and time for later reference. The recording mechanism may include a computer.

Another embodiment of a test apparatus in accordance with the principles of the claimed invention includes a mechanism for displaying measurements of displacement and time. The measurements may be displayed in graphic form. The display mechanism may include a computer.

It is also the purpose of the claimed invention to provide a test method for measuring at least one non-musical physical property of a test piece.

An embodiment of a test method in accordance with the principles of the claimed invention includes the steps of fixing a test piece to a frame, initiating free vibrations in the test piece, measuring the time-varying displacement of the test piece as it undergoes free vibration, and calculating at least one value of the physical property of the test piece.

Another embodiment of a test method in accordance with the principles of the claimed invention further includes the step of displaying the values of the physical property. The values may be displayed on a computer.

Another embodiment of a test method in accordance with the principles of the claimed invention further includes the step of supplying feedback for adjusting a manufacturing process based on the values of the physical property.

It is also the purpose of the claimed invention to provide a method for controlling a manufacturing process based on measured values of a physical property of a test piece produced by the manufacturing process.

An embodiment of a process control method in accordance with the principles of the claimed invention includes the steps of fixing a test piece produced by the process to a frame, initiating free vibrations in the test piece, measuring the time-varying displacement of the test piece as it undergoes free vibration, calculating at least one value of the physical property of the test piece, and adjusting the process based on the value of the physical property.

BRIEF DESCRIPTION OF THE DRAWINGS

Like reference numbers generally indicate corresponding elements in the figures.

DETAILED DESCRIPTION OF THE PREFERRED EMBODIMENT

Figure 1:
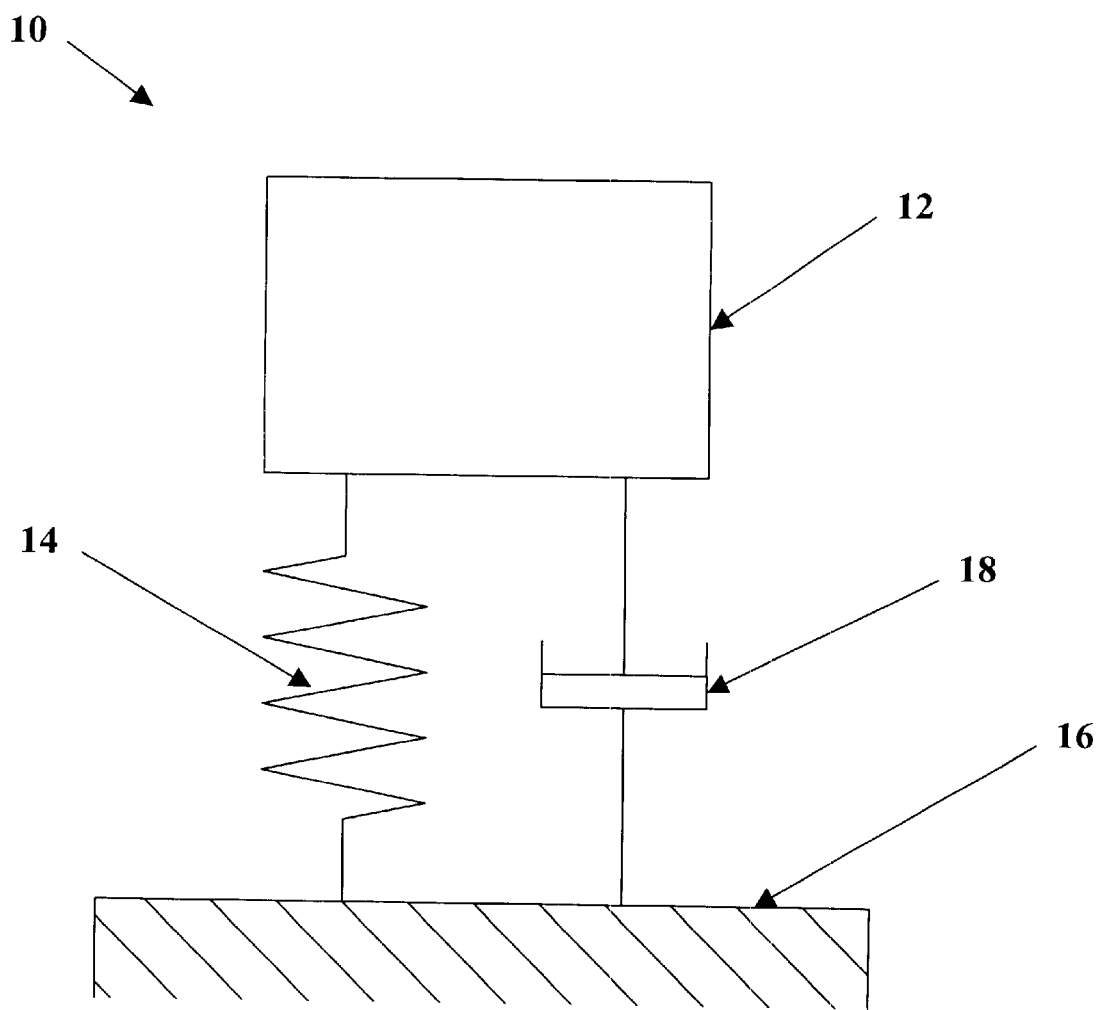
FIG. 1 is a schematic representation of a single degree of freedom mass-spring-damper system.
Figure 2:
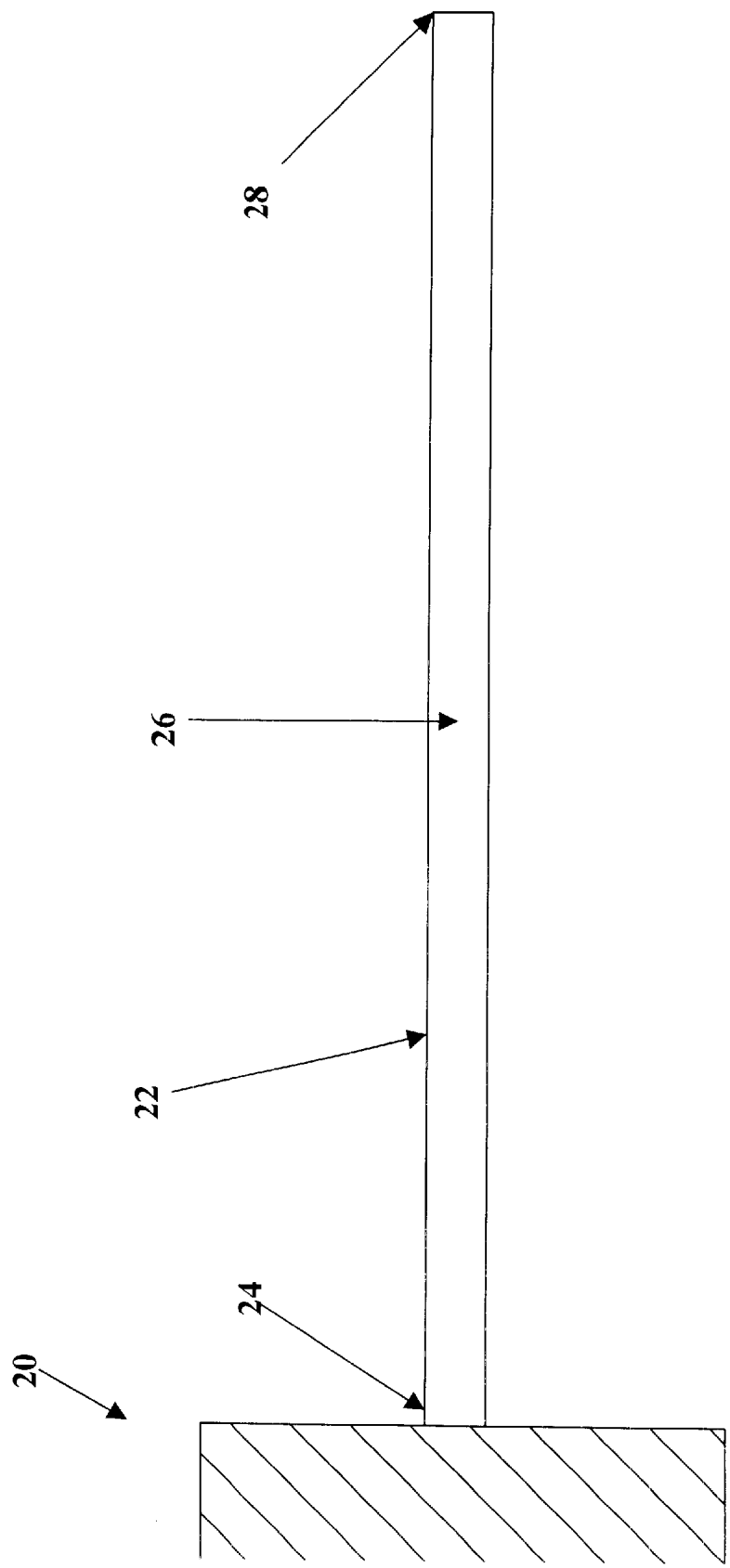
FIG. 2 is a side perspective view of a system with a longitudinal beam fixed at one end.
Figure 3:
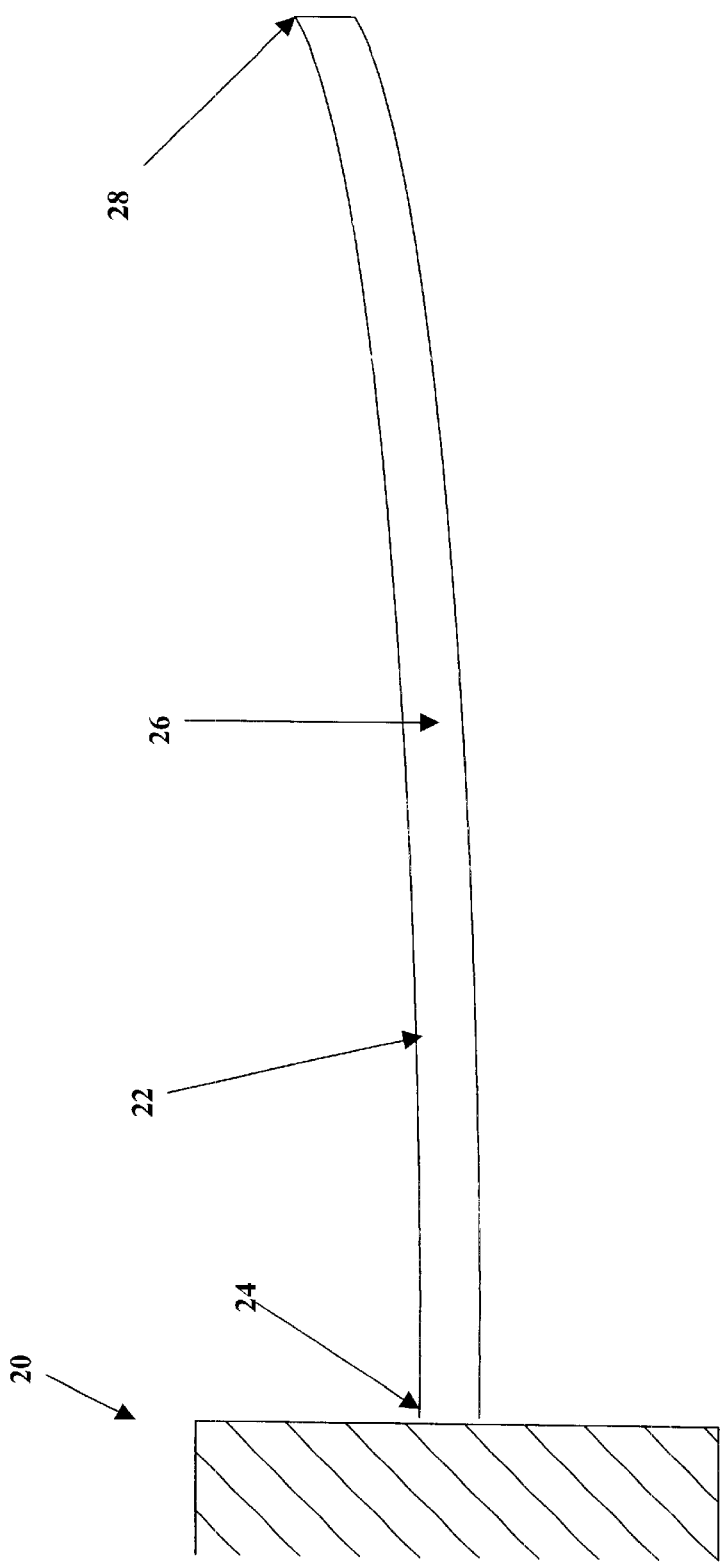
FIG. 3 is a side perspective view of the system of FIG. 2, shown with the beam undergoing a transverse longitudinal deflection.
Figure 4:
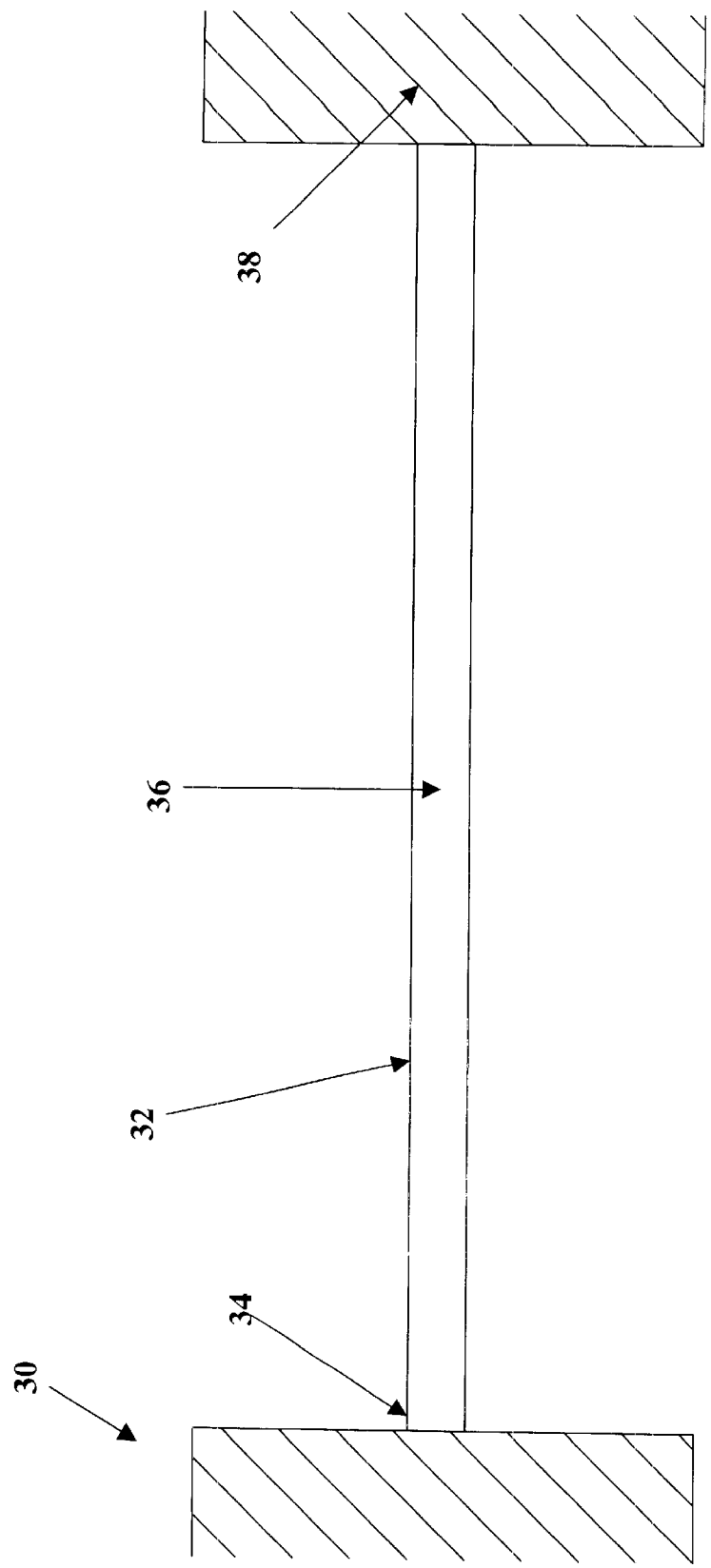
FIG. 4 is a side perspective view of a system with a longitudinal beam fixed at both ends.
Figure 5:
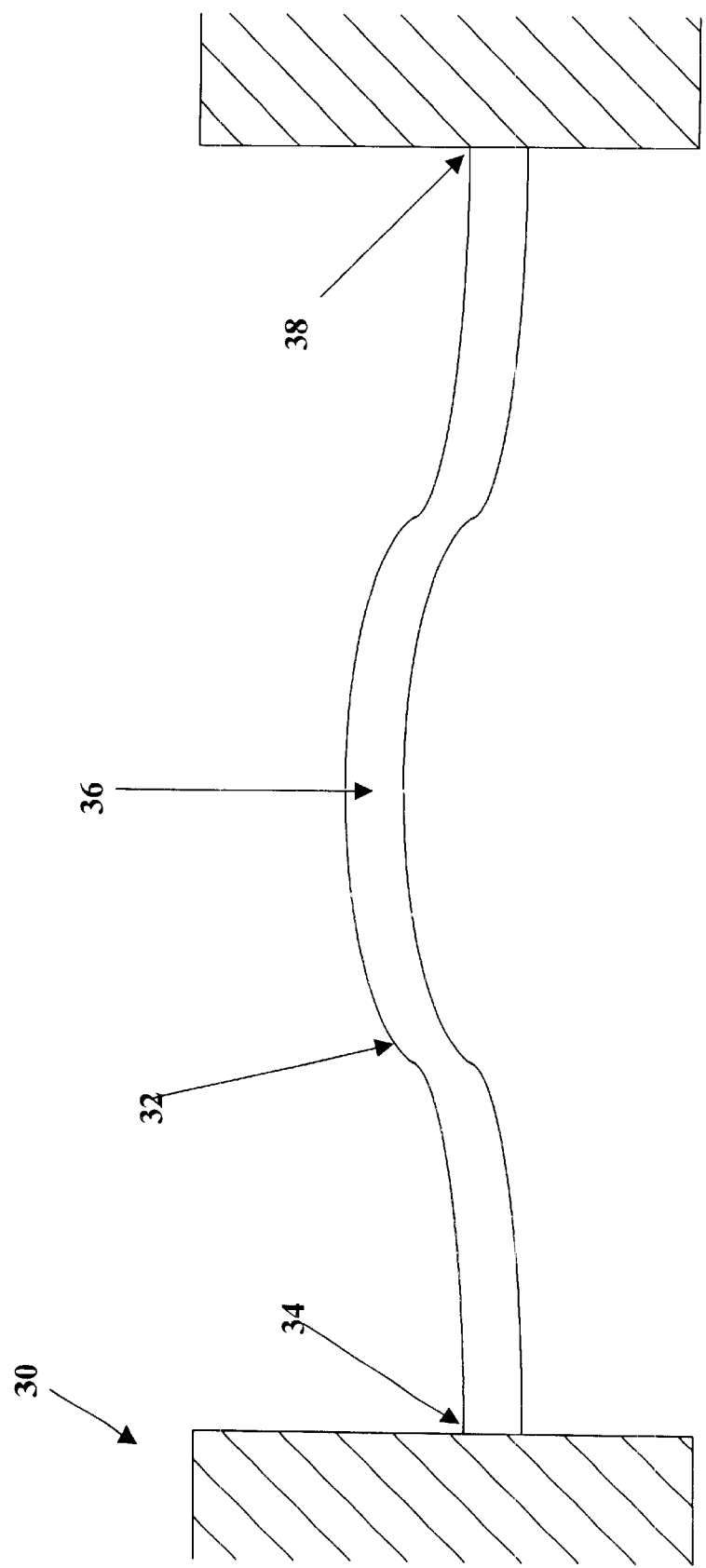
FIG. 5 is a side perspective view of the system of FIG. 4, shown with the beam undergoing a transverse longitudinal deflection.
Figure 6:
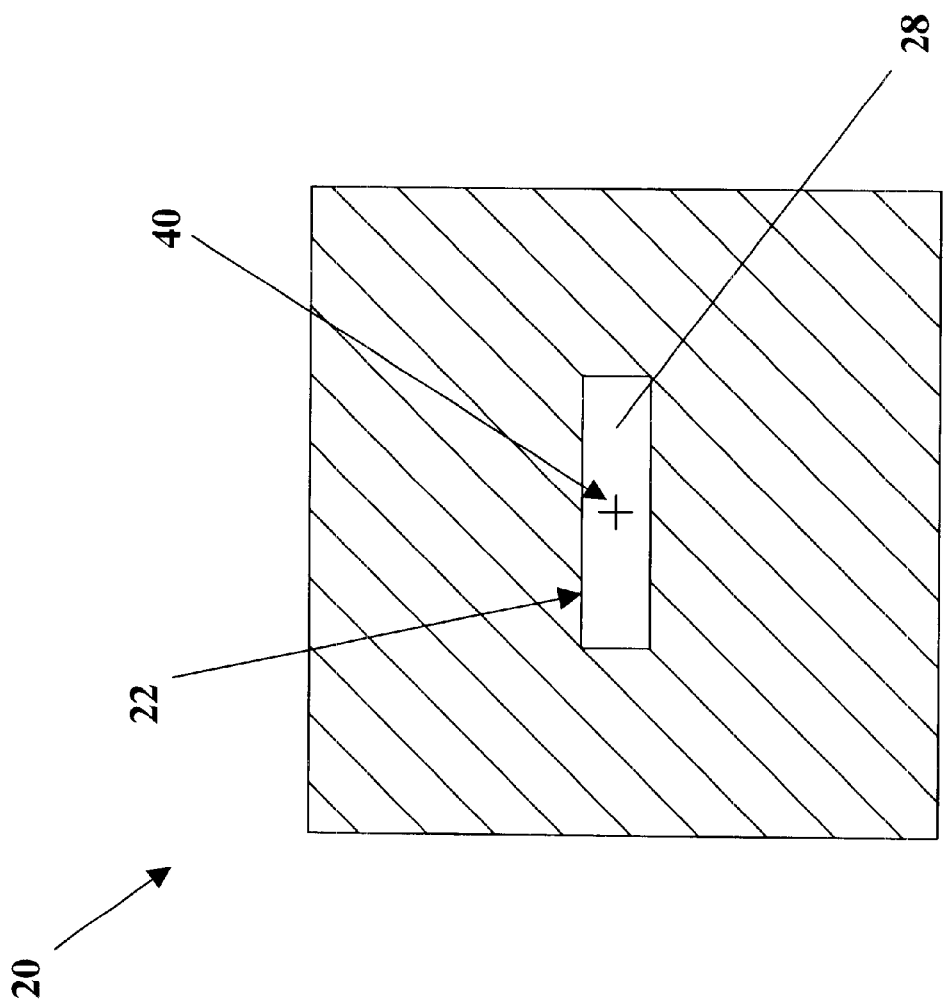
FIG. 6 is an end perspective view of the system of FIG. 2.
Figure 7:
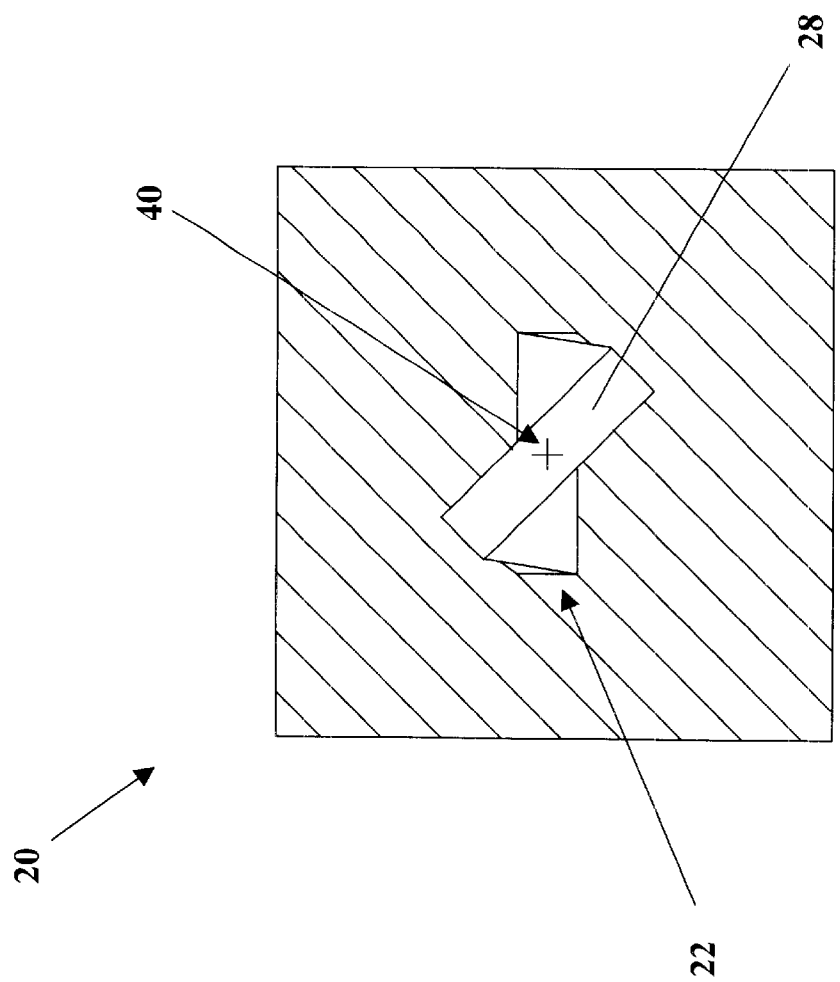
FIG. 7 is an end perspective view of the system of FIG. 2, shown with the beam undergoing a torsional deflection.
Figure 8:
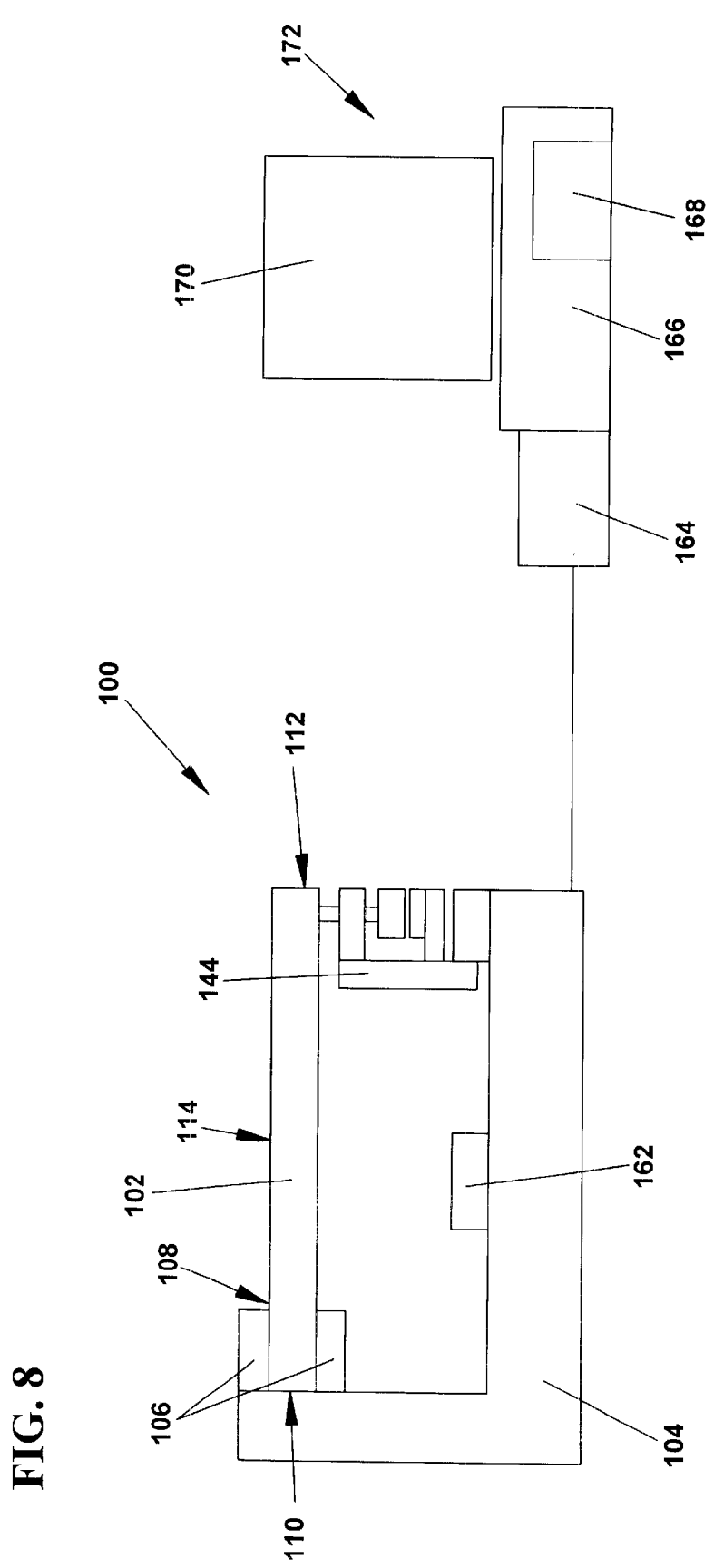
FIG. 8 is a perspective view of an embodiment of a test apparatus in accordance with the principles of the claimed invention, with a test piece therein.
Figure 9:
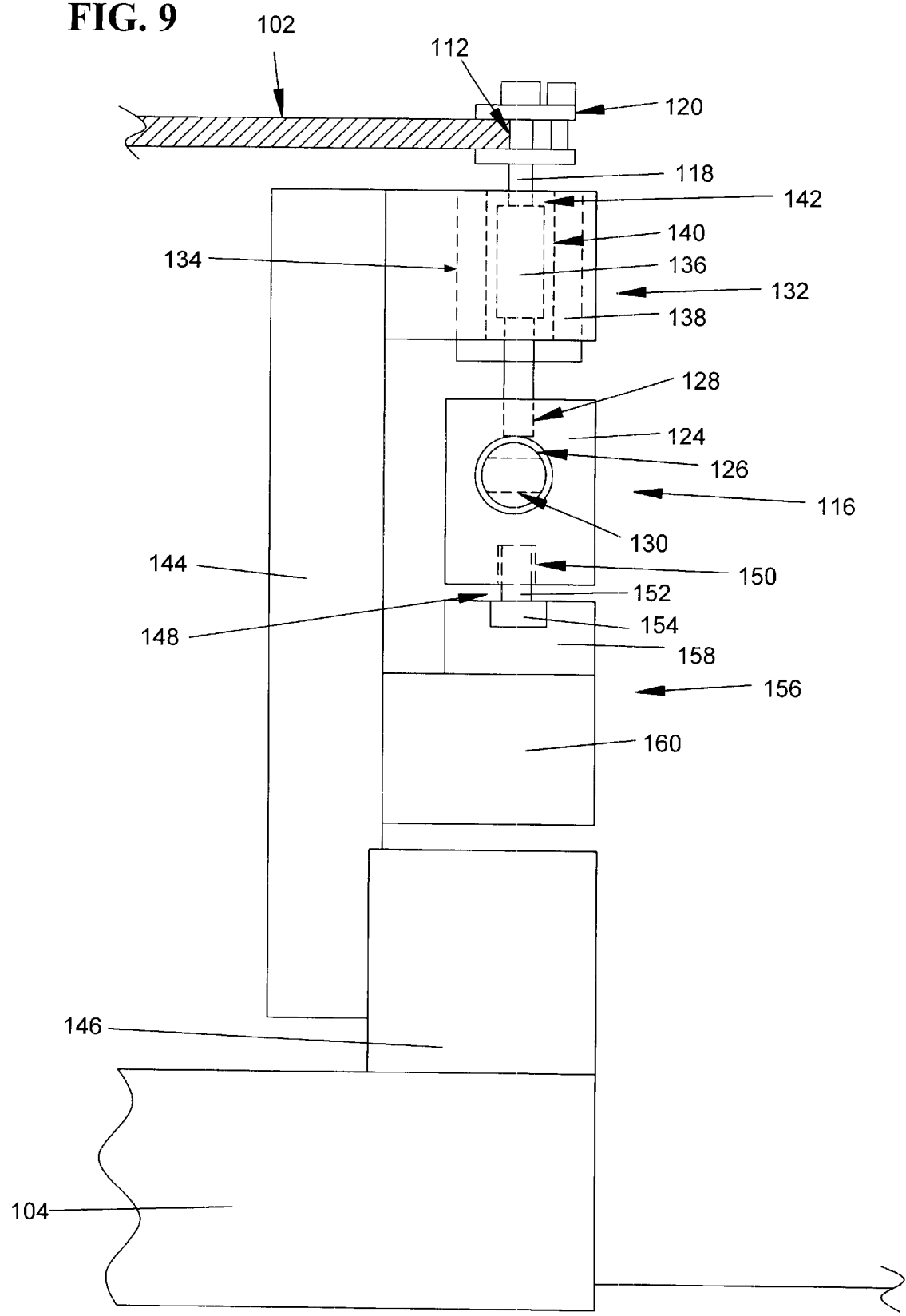
FIG. 9 is a perspective view of a load column of the embodiment shown in FIG. 8.
Figure 10:
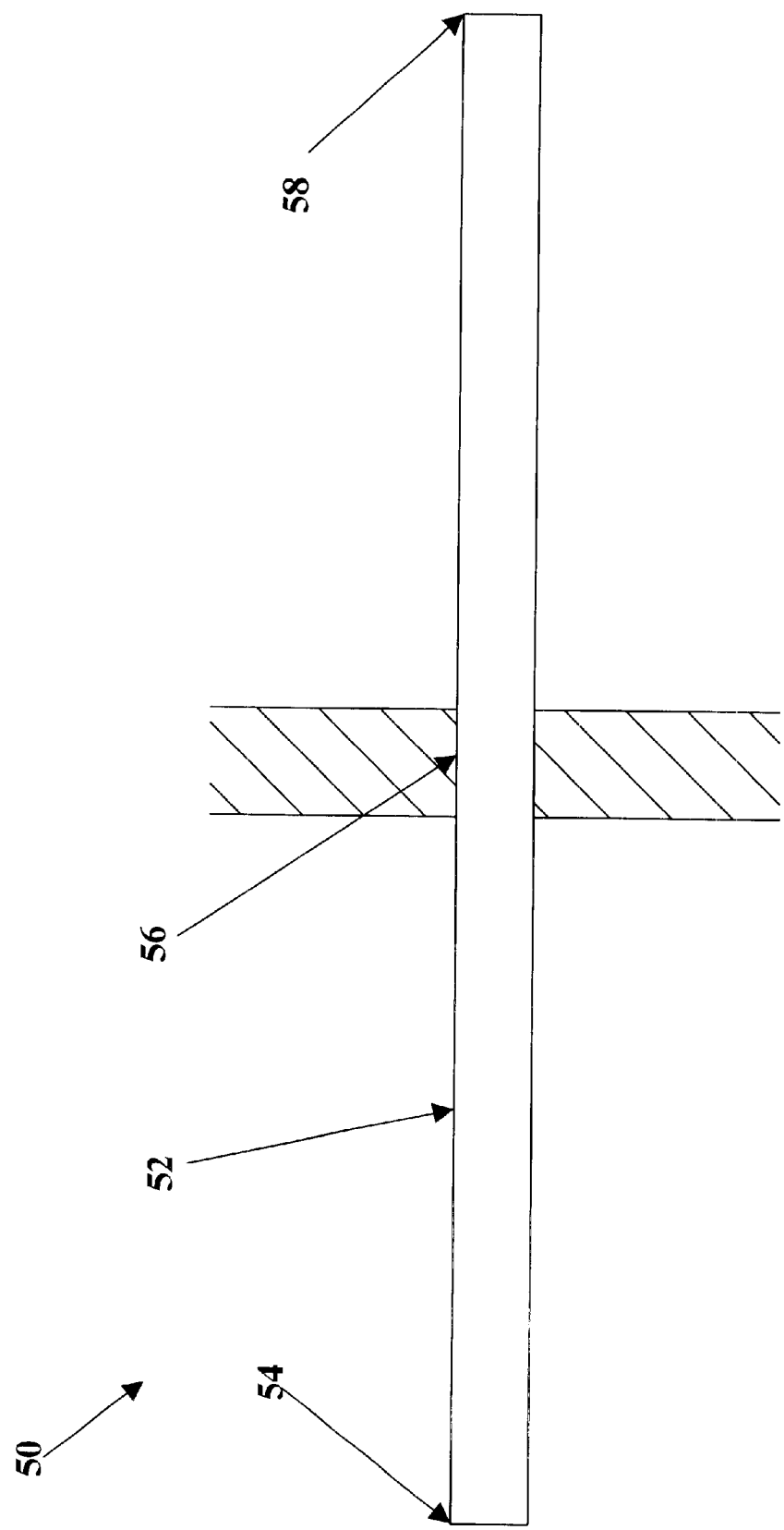
FIG. 10 is a side perspective view of a system with a longitudinal beam fixed at its center of mass.
Figure 11:
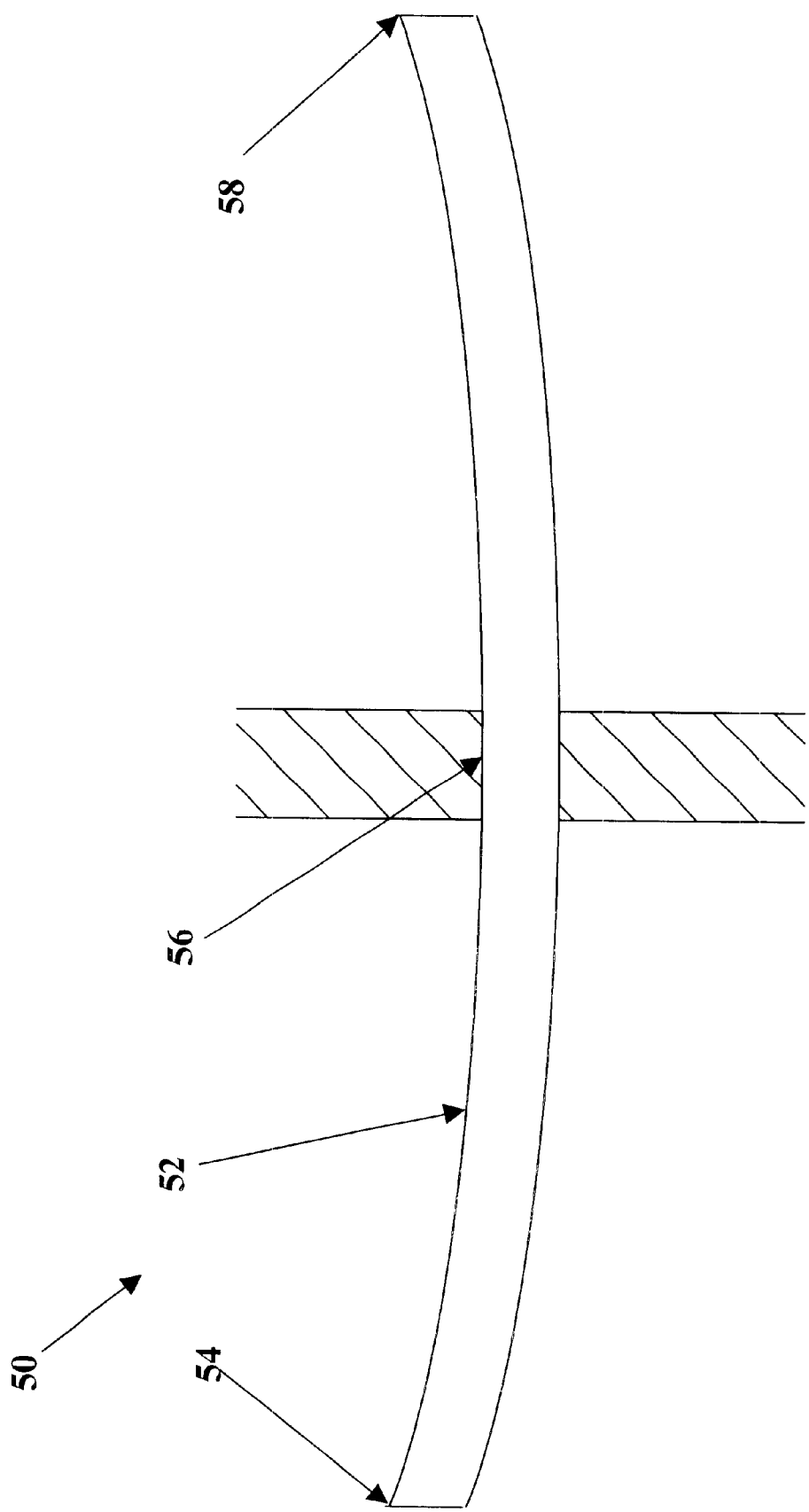
FIG. 11 is a side perspective view of the system of FIG. 10, shown with the beam undergoing a transverse longitudinal deflection.

Referring to FIGS. 8 and 9, an apparatus in accordance with the principles of the claimed invention includes a vibration decay evaluator (VDE) tester 100. A test piece 102 is fitted into the VDE tester 100.

The VDE tester 100 includes a frame 104. The frame 104 is substantially rigid, so as to avoid applying a significant damping force to the test piece 102. The frame 104 also has a natural vibrational frequency that is different from the anticipated natural vibrational frequency of any test piece 102 that is to be tested by the VDE tester 100. This is necessary because, if the natural vibrational frequency of the frame 104 is similar to that of a test piece 102, the vibrating test piece would transfer energy to the frame 104, thereby causing the amplitude of the vibrations in the test piece 102 to decrease more rapidly than they otherwise would.

The frame may be made of any sufficiently rigid material, including but not limited to metal, plastic, or wood.

The VDE tester 100 also includes fixing means 106 adapted to fix the test piece 102 to the frame 104 at at least one fixing point 108. The fixing means 106 hold the test piece 102 such that the fixing point 108 is prevented from moving when the test piece 102 undergoes free vibration.

As illustrated, the VDE tester 100 is adapted to utilize transverse longitudinal free vibrations in a test piece 102 in the shape of a substantially longitudinal beam. However, it will be appreciated by those knowledgeable in the art that this configuration is exemplary only, and that other configurations of VDE tester 100 and test piece 102 may be equally suitable, and may in particular be suitable for utilizing free vibrations other than transverse longitudinal free vibration, including but not limited to compressional free vibrations and torsional free vibrations.

A wide variety of fixing means 106 may be used with the claimed invention. In a preferred embodiment, the fixing means 106 include a mechanical clamp. In another preferred embodiment, the fixing means 106 include a water bladder clamp. However, it will be appreciated by those knowledgeable in the art that these are exemplary only, and that other fixing means 106 may be equally suitable.

As illustrated in FIG. 8, the fixing means 106 fix the test piece 102 at a first end 110. However, it will be appreciated by those knowledgeable in the art that this arrangement is exemplary only, and that other configurations may be equally suitable. Suitable configurations include but are not limited to fixing the first and second ends 110 and 112 of the test piece, and fixing the center of mass 114 of the test piece.

The VDE tester 100 also includes vibration initiating means 116 adapted to initiate free vibrations in the test piece 102.

An exemplary embodiment of vibration initiating means 116 is illustrated in FIG. 9. As shown therein, the vibration initiating means 116 include a pin 118 connected to the second end 112 of the test piece 102 by means of a clamp 120. The pin 118 and the clamp 120 are rigidly affixed to the test piece 102 so that moving the pin 118 likewise moves the second end 112 of the test piece 102.

The exemplary vibration initiation means 116 also include a pin release mechanism 122. As illustrated in FIG. 9, an exemplary pin release mechanism 122 includes a block 124 that is rigidly mounted to the frame 104, with a rotatable member 126 rotatably disposed within the block 124. The block 124 defines a first aperture 128 therein sized to freely accept the pin 118. The rotatable member 126 similarly defines a second aperture 130 therethrough sized to freely accept the pin 118. The rotatable member 126 is rotatable between a first position wherein the second aperture 130 is aligned with the first aperture 128 such that the first and second apertures 128 and 130 cooperate to accept the pin 118, and a second position wherein the second aperture 130 is not aligned with the first aperture 128 and does not accept the pin 118 therein.

The pin release mechanism 122 is positioned such that when the rotatable member 126 is in the second position, the pin 118 abuts against the rotatable member 126, whereby the second end 112 of the test piece 102 is deflected from an equilibrium position. When the rotatable member 126 moves from the second position to the first position, the deflection is released, whereupon transverse longitudinal free vibrations are initiated in the test piece 102.

As shown, the block 124 is mounted indirectly to the frame 104 via other elements. However, it will be appreciated by those knowledgeable in the art that this configuration is exemplary only, and that the block 124 could be mounted directly to the frame.

Similarly, it will be appreciated by those knowledgeable in the art that the aforementioned vibration initiating means 116 are exemplary only, and that other initiating means may be equally suitable. In particular, vibration initiating means that are not mounted to the frame may be equally suitable.

The VDE tester 100 also includes displacement measuring means 132 adapted to measure the displacement of the test piece 102.

An exemplary embodiment of the displacement measuring means 132 is illustrated in FIG. 9. As shown therein, the displacement measuring means 132 includes a linear voltage displacement transducer (LVDT) 134. LVDTs measure the position of a core moving through a body by detecting changes in the electrical properties of the core with respect to the body, and produce an electrical signal corresponding to the position of the core within the body. An LVDT does not require contact between the core and the body, and hence do not apply extraneous frictional forces to the apparatus. LVDTs are well known, and are not described further herein. The LVDT 134 includes a core 136 and a body 138. As illustrated in the exemplary embodiment of FIG. 9, the core 136 is rigidly connected to the pin 118 and moveable therewith, and the body 138 is rigidly mounted to the frame 104.

The body 138 defines a core aperture 140 therethrough sized so as to freely accept the core 136 therein. As the test piece 102 undergoes transverse longitudinal free vibration, the core 136 moves vertically within the core aperture 140 of the body 138. Because the core 136 is rigidly connected to the pin 118 which is in turn rigidly connected to the second end 112 of the test piece 102, the motion of the core 136 and consequently the signal output of the LVDT 134 corresponds to the motion of the second end 112 of the test piece 102.

It will be appreciated by those knowledgeable in the art that, for a system as illustrated in FIG. 8, wherein the test piece 102 is in the form of a longitudinal beam fixed at a first end 110, any additional mass affixed at the second end 112 will contribute its entire mass to $M_{sensor}$. That is, as noted previously with respect to Equation 45 and subsequently, k is 1. The nature of the individual component or components that contribute the mass is not relevant to the vibration of the test piece 102. Thus, for purposes of calculation, in the exemplary embodiment shown in FIG. 9 the clamp 120, the pin 118, and the LVDT core 136 may all be collectively considered to be the sensor 142, and the combined mass thereof is $M_{sensor}$. It will be appreciated by those knowledgeable in the art that the embodiment shown in FIG. 9 is exemplary only, and that the components that contribute to $M_{sensor}$ for any alternate displacement measuring means 132 will depend on the structure and nature of the particular displacement measuring means 132. It will furthermore be appreciated that for certain displacement measuring means 132, including but not limited to ultrasonic or laser rangefinding mechanisms, no additional components will necessarily be affixed to the test piece 102, and that in such a case $M_{sensor}$ will be zero.

As shown in FIG. 9, the body 138 is mounted indirectly to the frame 104 via a column spine 144 and a column mount 146. However, it will be appreciated by those knowledgeable in the art that this configuration is exemplary only, and that the body 138 could be mounted directly to the frame.

Similarly, it will be appreciated by those knowledgeable in the art that the aforementioned displacement measuring means 132 are exemplary only, and that other initiating means may be equally suitable. In particular, displacement measuring means that are not mounted to the frame may be equally suitable.

In a preferred embodiment of the VDE tester 100, the displacement measuring means 132 are adapted to obtain measurements of displacement at least 1,000 times per second. In a more preferred embodiment of the VDE tester 100, the displacement measuring means 132 are adapted to obtain measurements of displacement at least 10,000 times per second. In a still more preferred embodiment of the VDE tester 100, the displacement measuring means 132 are adapted to obtain measurements of displacement at least 100,000 times per second.

An exemplary embodiment of the VDE tester 100 includes initiation control means 148 adapted for controlling the initial amplitude of the free vibrations. As illustrated in FIG. 9, the initiation control means 148 include an adjustment aperture 150 defined in the block 124 of the vibration initiating means 116 and an adjustment screw 152 rotatably disposed at least partially within the adjustment aperture 150. The adjustment aperture 150 and the adjustment screw 152 are threaded so as to cooperate with one another, such that rotation of the adjustment screw 152 causes a vertical displacement of the block 124. A vertical displacement of the block 124 in turn causes a change in the position occupied by the pin 118 when the rotatable member 126 is in the second position, that is, when the second aperture 130 is not aligned with the first aperture 128 and does not accept the pin 118 therein. Because the pin 118 is rigidly affixed to the test piece 102, a change in the position of the pin 118 results in a change in the initial deflection of the test piece 102. Thus, by rotating the adjustment screw 152, the deflection of the test piece 102 at the start of free vibration may be controlled.

As shown in FIG. 9, the adjustment screw 152 is mounted to the frame 104 via other elements. However, it will be appreciated by those knowledgeable in the art that this configuration is exemplary only, and that the adjustment screw 152 could be mounted directly to the frame.

An exemplary embodiment of the initiation control means 148 includes deflection measuring means 154 adapted for measuring an initial deflection of the test piece 102. As illustrated in FIG. 9, the deflection measuring means 154 include a micrometer mechanically engaged with the adjustment screw 152, so as to enable convenient and accurate measurement of the vertical displacement of the block 124, and thus also the initial deflection of the test piece 102.

It will be appreciated by those knowledgeable in the art that the aforementioned initiation control means 148 are exemplary only, and that other initiation control means may be equally suitable. In particular, it will be appreciated that deflection measuring means 154 other than a micrometer may be equally suitable for measuring initial deflection, or that the deflection measuring means 154 may be omitted entirely. Furthermore, it will be appreciated that for certain embodiments of the VDE tester, including but not limited to embodiments adapted only for a fixed initial deflection, initiation control means 148 will not be included.

An exemplary embodiment of the VDE tester 100 includes load measuring means 156 adapted to measure the load applied to the test piece 102 during initial deflection. As illustrated in FIG. 9, the load measuring means 156 include a load cell 158. Load cells are well known, and are not described further herein. The load cell 158 is rigidly affixed to a load cell mount 160, which is in turn rigidly affixed to the column spine 144. As previously noted, in the embodiment of FIG. 9 the column spine 144 is rigidly affixed to the column mount 146, which is rigidly affixed to the frame 104. Thus, the load cell 158 is rigidly affixed to the frame 104. The load cell 158 is engaged with the initiating means 116, such that the force between the initiating means 116 and the frame 104, and hence between the test piece 102 and the frame 104 during initial displacement, may be measured by the load cell 158.

As shown, the load cell 158 is mounted to the frame via other elements. However, it will be appreciated by those knowledgeable in the art that this configuration is exemplary only, and that the load cell 158 could be mounted directly to the frame. Likewise, as shown the load cell 158 is engaged with the initiating means 116 via the initiation control means 148. It will be appreciated that the load cell 158 could be engaged with the initiating means directly, or via other components.

Similarly, it will be appreciated by those knowledgeable in the art that the aforementioned load measuring means 156 are exemplary only, and that other load measuring means may be equally suitable. Furthermore, it will be appreciated that certain embodiments of the VDE tester 100, including but not limited to embodiments adapted for applying a fixed load at initial deflection, will not include load measuring means 156.

Additionally, it will be appreciated that certain embodiments of the VDE tester 100, including but not limited to embodiments adapted for initiating free vibrations of a fixed initial amplitude, will not include initiation control means 148.

The VDE tester 100 also includes time measuring means 162 adapted to measure time during free vibration. The time measuring means 162 are in communication with the displacement measuring means 132, such that the displacement of the test piece 102 may be determined for a particular time.

As illustrated, the time measuring means 162 are mounted directly to the frame 104. However, it will be appreciated by those knowledgeable in the art that this configuration is exemplary only, and that the time measuring means 162 may be mounted differently, or may not be mounted at all. The time measuring means 162 may be physically remote from the frame 104, so long as they are in communication with the displacement measuring means 132.

In a preferred embodiment of the VDE tester 100, the time measuring means 162 are adapted to obtain measurements of displacement at least 1,000 times per second. In a more preferred embodiment of the VDE tester 100, the time measuring means 162 are adapted to obtain measurements of displacement at least 10,000 times per second. In a still more preferred embodiment of the VDE tester 100, the time measuring means 162 are adapted to obtain measurements of displacement at least 100,000 times per second.

A wide variety of time-measuring means 162 may be used with the claimed invention. In a preferred embodiment, the time measuring means 162 include a digital timing circuit. This is convenient, in that digital timing circuits are compact, inexpensive, and durable. However, it will be appreciated by those knowledgeable in the art that this configuration is exemplary only, and that other time measuring means 162 may be equally suitable. Time measuring means are well known, and are not described further herein.

An exemplary embodiment of the VDE tester 100 includes collecting means 164 adapted to collect measurements of displacement and time from the displacement measuring means 132 and the time measuring means 162. As illustrated in FIG. 8, the collecting means 164 are part of a computer 172. In a preferred embodiment of the claimed invention, the collecting means 164 include a plug-in data acquisition card installed in a computer 172. This is advantageous, in that such cards are reliable, simple to use, and widely available. However, it will be appreciated by those knowledgeable in the art that this configuration is exemplary only, and that other collecting means 164 may be equally suitable. Collecting means are well known, and are not described further herein.

It will be appreciated by those knowledgeable in the art that the measurements of displacement and time may be collected in a variety of forms, including but not limited to digital and analog electrical output signals from the displacement measuring means 132 and the time measuring means 162.

An exemplary embodiment of the VDE tester 100 includes processing means 166 adapted to process measurements of displacement and time in order to determine other information therefrom. For example, the processing means 166 are advantageously adapted to generate at least one value of at least one physical property of the test piece 102, including but not limited to $C_L$, $K_L$ and $E_L$. Advantageously, the processing means 166 are adapted to generate a plurality of values of at least one physical property of the test piece.

As illustrated in FIG. 8, the processing means 166 are part of a computer 172. In a preferred embodiment of the claimed invention, the processing means 166 include the CPU of a computer 172. In another preferred embodiment of the claimed invention, the processing means 166 further include a software application adapted to run on the CPU of a computer 172. However, it will be appreciated by those knowledgeable in the art that these configurations are exemplary only, and that other processing means 166 may be equally suitable. Processing means are well known, and are not described further herein.

An exemplary embodiment of the VDE tester 100 includes recording means 164 adapted to record measurements of displacement and time from the displacement measuring means 132 and the time measuring means 162. Advantageously, the recording means 168 are adapted to record processed information from the processing means 166 as well. As illustrated in FIG. 8, the recording means 168 are part of a computer 172. In a preferred embodiment of the claimed invention, the recording means 168 include a hard drive of a computer 172. This is advantageous, in that hard drives are widely available. However, it will be appreciated by those knowledgeable in the art that this configuration is exemplary only, and that other recording means 168 may be equally suitable, including but not limited to floppy drives, CD drives, and printers. Recording means are well known, and are not described further herein.

An exemplary embodiment of the VDE tester 100 includes display means 170 adapted to display measurements of displacement and time from the displacement measuring means 132 and the time measuring means 162. Advantageously, the display means 170 are adapted to display processed information from the processing means 166 as well, and/or to display recorded information from the recording means 168. As illustrated in FIG. 8, the display means 170 are part of a computer 172. In a preferred embodiment of the claimed invention, the display means 170 include a monitor of a computer 172. This is advantageous, in that computer monitors are widely available. However, it will be appreciated by those knowledgeable in the art that this configuration is exemplary only, and that other display means 170 may be equally suitable, including but not limited to printers, plotters, LED displays, and indicator lights. Display means are well known, and are not described further herein.

In a preferred embodiment of the VDE tester, the collecting means 164, processing means 166, recording means 168, and display means 170 are all parts of a single computer 172. In another preferred embodiment of the claimed invention, the computer 172 is a laptop computer. These configurations are advantageous, in that a laptop computer that includes all of the collecting means 164, processing means 166, recording means 168, and display means 170 is convenient and easily portable. However, it will be appreciated by those knowledgeable in the art that this configuration is exemplary only. Other computers 172 may be equally suitable for use with the claimed invention. Furthermore, the collecting means 164, processing means 166, recording means 168, and display means 170 need not be part of a single computer, and may for example be parts of several different computers connected via a network, or may be stand-alone devices not part of any computer.

As shown, the collecting means 164, processing means 166, recording means 168, and display means 170 are separate from the frame 104. However, it will be appreciated that this configuration is exemplary only, and that some or all of the collecting means 164, processing means 166, recording means 168, and display means 170 may be attached to the frame. Furthermore, it will be appreciated that some or all of the collecting means 164, processing means 166, recording means 168, and display means 170 may be remote from the frame 104. For example, it may be advantageous for certain applications to transmit time and displacement measurements some distance, i.e. via an internet connection, prior to collecting, processing, recording, and displaying them. Additionally, it will be appreciated that a plurality of collecting means 164, processing means 166, recording means 168, and display means 170 may be used to collect, process, record, and display the same measurements of time and displacement, either simultaneously or at different times.

It will be appreciated by those knowledgeable in the art that although collecting means 164, processing means 166, recording means 168, and display means 170 may be advantageous for certain exemplary embodiments of the VDE tester 100, some or all of the collecting means 164, processing means 166, recording means 168, and display means 170 may be omitted entirely from certain other exemplary embodiments. For example, it would be possible to determine values of physical properties from the measurements produced by the displacement measuring means 132 and the time measuring means 162 manually, without additional mechanisms.

In order to determine one or more non-musical properties of the test piece 102, the test piece 102 is placed in the VDE tester 100, and free vibrations are initiated in the test piece 102 via the initiating means 116. The displacement of the test piece 102 over time is measured with the displacement measuring means 132 and the time measuring means 162. Physical properties, including but not limited to the damping coefficient C, the stiffness coefficient K, and the Young's Modulus E, may then be calculated from the displacement and time measurements. For example, values of $C_L$, $K_L$ and $E_L$ for a test piece 102 substantially in the form of longitudinal beam may be calculated according to Equations 49, 50, and 51. It will be appreciated that, although Equations 49, 50, and 51 are specific to a longitudinal beam, this is exemplary only. Values of physical properties for test pieces of other configurations may be calculated similarly using analogous equations.

As has been previously noted, many systems of interest have a damping ratio $\zeta$ that is substantially less than 1. It will be appreciated by those knowledgeable in the art that in such a case, energy is lost from the system slowly, and therefore a single decay cycle of free vibrations typically consists of many individual vibrations. As a result, useful values of one or more physical properties can be generated from a single decay cycle of free vibrations. In practice, it is therefore possible to obtain values for physical properties by initiating free vibrations only once in a particular test piece. It will also be appreciated, however, that as initiating free vibrations is non-destructive, free vibrations could just as well be initiated any number of times in a particular test piece, rather than only once.

Furthermore, as previously described, as free vibrations decay their amplitude decreases. Thus, the peak displacement decreases over the course of a decay cycle. It will be appreciated by those knowledgeable in the art that a plurality of values of one or more physical properties may be calculated from a single initiation of free vibrations in a test piece. Furthermore, it will be appreciated that by calculating a values of physical properties over a range of amplitudes as the vibrations decay, a dynamic range of values of the properties over a range of displacements may be determined. For example, $K_L$ may be determined over a range of strains, rather than at a particular point. However, it will also be appreciated that it is not necessary to calculate a dynamic range of values for a physical property, and that for certain applications it may be advantageous to calculate only a few or even only a single value.

For many common materials, free vibrations occur with a frequency of on the order of hundreds of cycles per second. Therefore, it is possible to gather substantial data within a relatively short time, a matter of few seconds. In addition, given the speed of known processing means, it is possible to determine at least one value of at least one physical property from measurements of time and displacement in on the order of one second or less. Thus, according to the claimed invention, for common materials it is possible to obtain values of physical properties no more than 5 seconds after initiation of free vibrations in the test piece 102.

Advantageously, the VDE tester 100 may be used to provide feedback for a manufacturing process. It will be appreciated by those knowledgeable in the art that, once information is derived by use of the VDE tester 100 regarding the test piece 102, this information may be used to adjust a manufacturing process used to produce the test piece. In this way, manufacturing processes may be controlled so as to consistently produce optimum product.

It will also be appreciated that, because the VDE tester 100 is operates on principles that do not depend on the internal geometry of the test piece, the VDE tester 100 is insensitive to the shape and configuration of the test piece 102. Thus, the normal output of a manufacturing process may be tested on the VDE tester 100.

In a preferred embodiment of the VDE tester 100, the processing means 166 are adapted to generate feedback automatically based on calculated values of physical properties. This is advantageous, in that it enables persons without extensive training in the effects of adjusting process parameters to successfully adjust a manufacturing process. However, it will be appreciated that this is exemplary only, and that for certain applications it may be desirable to provide feedback from other sources, or to omit feedback altogether.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An apparatus for measuring at least one non-musical physical property of a test piece having a stable geometry, comprising:

a frame having a natural vibrational frequency different from a free vibration of the test piece;

fixing means adapted to removably fix at least one fixing point of the test piece;

initiating means adapted to initiate the free vibration in the test piece resulting in a vibrating test piece;

displacement measuring means adapted to obtain measurements of a displacement of said vibrating test piece;

time measuring means in communication with said displacement measuring means, said time measuring means being adapted to obtain a measurement of time.

2. The apparatus as claimed in claim 1, wherein said initiating means are adapted to apply a deflection to the test piece, and wherein said initiating means are adapted to release said deflection whereby the free vibrations are initiated in the test piece.

3. The apparatus as claimed in claim 1, wherein the free vibrations are transverse longitudinal vibrations, wherein the displacement is transverse to a longitudinal axis of the test piece.

4. The apparatus as claimed in claim 1, further comprising collecting means adapted for collecting said measurements of displacement and time.

5. The apparatus as claimed in claim 4, wherein said collecting means comprise a computer.

6. The apparatus as claimed in claim 1, further comprising processing means adapted for processing said measurements of displacement and time.

7. The apparatus as claimed in claim 6, wherein said processing means comprise a computer.

8. The apparatus as claimed in claim 1, further comprising recording means adapted for recording said measurements of displacement and time.

9. The apparatus as claimed in claim 8, wherein said recording means comprise a computer.

10. The apparatus as claimed in claim 1, further comprising display means adapted for displaying said measurements of displacement and time.

11. The apparatus as claimed in claim 10, wherein said display means comprise a computer monitor.

12. The apparatus as claimed in claim 1, wherein said displacement measuring means and said time measuring means are adapted to obtain measurements at least 1000 times per second.

13. The apparatus as claimed in claim 1, wherein said fixing means are adapted to fix a generally longitudinal test piece at a first end of the test piece.

14. The apparatus as claimed in claim 13, wherein said fixing means are adapted to fix the test piece at the first end and a second end of the test piece.

15. The apparatus as claimed in claim 1, wherein said fixing means are adapted to fix a generally longitudinal test piece at a center point generally coinciding with a center of mass of the test piece.

16. The apparatus as claimed in claim 1, wherein said fixing means are adapted to releasably fix said at least one fixing point of the test piece.

17. The apparatus as claimed in claim 1, wherein said fixing means comprise a mechanical clamp.

18. The apparatus as claimed in claim 1, wherein said fixing means comprise a water bladder clamp.

19. The apparatus as claimed in claim 1, wherein said fixing means comprise an adhesive.

20. The apparatus as claimed in claim 2, wherein said initiating means are adapted to be actuatable between a first position wherein said deflection of the test piece is not enabled, and a second position wherein said deflection of the test piece is enabled.

21. The apparatus as claimed in claim 20, wherein said initiating means comprises:

a pin releasably connected to the test piece, said pin being generally perpendicular to a length of the test piece, said pin being adapted to apply said deflection the test piece, said deflection being generally transverse to said length of the test piece; and a rotatable member connected to said frame, said rotatable member being rotatable about an axis generally perpendicular to said pin, said rotatable member being adapted to engage said pin so as to enable said pin to apply said deflection to the test piece, said rotatable member defining an aperture therein sized so as to receive said pin in a non-interfering fit;

wherein when said initiating means is in said first position said rotatable member is oriented such that said aperture receives said pin, whereby said pin is not enabled to apply said deflection to the test piece; and wherein when said initiating means is in said second position said rotatable member is oriented such that said aperture does not receive said pin, whereby said pin is enabled to apply said deflection to the test piece.

22. The apparatus as claimed in claim 1, wherein said displacement measuring means are non-contact measuring means.

23. The apparatus as claimed in claim 1, wherein said displacement measuring means comprise a linear variable displacement transducer.

24. The apparatus as claimed in claim 23, wherein said linear variable displacement transducer comprises a core, core mounting means for releasably mounting said core to the test piece, and a body connected to said frame, said body being suitable for accepting said core therein.

25. The apparatus as claimed in claim 2, further comprising load measuring means connected to said initiating means, said load measuring means being adapted to obtain measurements of a load applied to the test piece during said deflection of the test piece.

26. The apparatus as claimed in claim 25, wherein said load measuring means comprise a load cell.

27. The apparatus as claimed in claim 2, further comprising deflection control means connected to said initiating means, said deflection control means being adapted to control said deflection of the test piece.

28. The apparatus as claimed in claim 25, wherein said deflection control means comprise a micrometer.

29. The apparatus as claimed in claim 1, wherein said time measuring means comprise a digital timing circuit.

30. A method for measuring at least one non-musical physical property of a test piece having a stable geometry, comprising the steps of:

removably fixing the test piece to a frame at at least one fixing point, said frame having a natural vibrational frequency different from a free vibration of the test piece;

initiating the free vibration in the test piece;

measuring a time-varying displacement of the test piece during the free vibration; and calculating at least one value for said at least one physical property from the time-varying displacement.

31. The method according to claim 30, wherein a plurality of values are calculated for said at least one physical property of the test piece from the time-varying displacement.

32. The method according to claim 30, further comprising the step of displaying said at least one value.

33. The method according to claim 32, wherein said at least one value is displayed graphically.

34. The method according to claim 30, wherein said at least one value is calculated using a computer.

35. The method according to claim 32, wherein said at least one value is displayed using a computer.

36. The method according to claim 30, wherein said at least one physical property is a Young's Modulus of the test piece.

37. The method according to claim 30, wherein said at least one physical property is a damping coefficient of the test piece.

38. The method according to claim 30, wherein said at least one physical property is a stiffness coefficient of the test piece.

39. The method according to claim 36, further comprising the step of mounting a sensor to the test piece at a displacement measuring point, said sensor being adapted for measuring the time-varying displacement of the test piece, and wherein the at least one value of the Young's Modulus is calculated according to $$E = \frac{4\pi^2 L^3 (kM_{sensor} + k' M_{test})}{k'' T_d^2 I \left(1 - \left(\frac{\ln\left(\frac{y_0}{y_{(0+n)}}\right)}{2\pi n}\right)^2\right)}$$

wherein

E is the Young's Modulus of the test piece

L is a length between said at least one fixing point and said displacement measuring point k is a geometric coefficient corresponding to a position of said displacement measuring point $M_{sensor}$ is a mass of said sensor at said displacement measuring point k' is a geometric coefficient corresponding to a position of said at least one fixing point on the test piece $M_{test}$ is a mass of the test piece k" is a geometric coefficient corresponding to a an orientation of the test sample relative to said at least one fixing point $T_d$ is a damped natural period of the free vibrations I is a moment of inertia of the test piece about said at least one fixing point $y_0$ is the displacement of the test piece after zero free vibrations $y_{(0+n)}$ is the displacement of the test piece after zero plus n free vibrations n is a number of free vibrations.

40. The method according to claim 36, further comprising the step of mounting a sensor to the test piece at a displacement measuring point, said sensor being adapted for measuring the time-varying displacement of the test piece, and wherein:

the test piece is fixed to said frame at a first end of the test piece;

said displacement measuring point is at a second end of the test piece opposite the first end;

the free vibrations are initiated at a point generally coincidental with said displacement measuring point; and the at least one value of the Young's Modulus is calculated according to $$E = \frac{4\pi^2 L^3 (M_{sensor} + (0.2357) M_{test})}{3 T_d^2 I \left(1 - \left(\frac{\ln\left(\frac{y_0}{y_{(0+n)}}\right)}{2\pi n}\right)^2\right)}$$

wherein

E is the Young's Modulus of the test piece

L is a length between said at least one fixing point and said displacement measuring point $M_{sensor}$ is a mass of said sensor $M_{test}$ is a mass of the test piece $T_d$ is a damped natural period of the free vibrations I is a moment of inertia of the test piece about said at least one fixing point $y_0$ is the displacement of the test piece after zero free vibrations $y_{(0+n)}$ is the displacement of the test piece after zero plus n free vibrations n is a number of free vibrations.

41. The method according to claim 36, further comprising the step of mounting a sensor to the test piece at a displacement measuring point, said sensor being adapted for measuring the time-varying displacement of the test piece, and wherein the test piece is fixed to said frame at a first end of the test piece and at a second end of the test piece opposite the first end;

said displacement measuring point generally coincides with a center of mass of the test piece;

the free vibrations are initiated at a point generally coincidental with said displacement measuring point; and the at least one value of the Young's Modulus is calculated according to $$E = \frac{4\pi^2 L^3 (M_{sensor} + (0.3610) M_{test})}{192 T_d^2 I \left(1 - \left(\frac{\ln\left(\frac{y_0}{y_{(0+n)}}\right)}{2\pi n}\right)^2\right)}$$

wherein

E is the Young's Modulus of the test piece

L is a length between said at least one fixing point and said displacement measuring point $M_{sensor}$ is a mass of said sensor $M_{test}$ is a mass of the test piece $T_d$ is a damped natural period of the free vibrations I is a moment of inertia of the test piece about said at least one fixing point $y_0$ is the displacement of the test piece after zero free vibrations $y_{(0+n)}$ is the displacement of the test piece after zero plus n free vibrations n is a number of free vibrations.

42. The method according to claim 37, further comprising the step of mounting a sensor to the test piece at a displacement measuring point, said sensor being adapted for measuring the time-varying displacement of the test piece, and wherein the at least one value of the damping coefficient is calculated according to $$C_L = \left(\frac{4\pi(k M_{sensor} + k' M_{test})}{T_d}\right) \frac{\ln\left(\frac{y_0}{y_{(0+n)}}\right)}{\sqrt{1 - \left(\frac{\ln\left(\frac{y_0}{y_{(0+n)}}\right)}{2\pi n}\right)^2}}$$

wherein

C is the damping coefficient of the test piece k is a geometric coefficient corresponding to a position of said displacement measuring point $M_{sensor}$ is a mass of said sensor k' is a geometric coefficient corresponding to a position of said at least one fixing point on the test piece $M_{test}$ is a mass of the test piece $T_d$ is a damped natural period of the free vibrations $y_0$ is the displacement of the test piece after zero free vibrations $y_{(0+n)}$ is the displacement of the test piece after zero plus n free vibrations n is a number of free vibrations.

43. The method according to claim 37, further comprising the step of mounting a sensor to the test piece at a displacement measuring point, said sensor being adapted for measuring the time-varying displacement of the test piece, and wherein:

the test piece is fixed to said frame at a first end of the test piece;

said displacement measuring point is at a second end of the test piece opposite the first end;

the free vibrations are initiated at a point generally coincidental with said displacement measuring point; and the at least one value of the damping coefficient is calculated according to $$C = \left(\frac{4\pi(M_{sensor} + (0.2357) M_{test})}{T_d}\right) \frac{\ln\left(\frac{y_0}{y_{(0+n)}}\right)}{\sqrt{1 - \left(\frac{\ln\left(\frac{y_0}{y_{(0+n)}}\right)}{2\pi n}\right)^2}}$$

wherein

C is the damping coefficient of the test piece $M_{sensor}$ is a mass of said sensor $M_{test}$ is a mass of the test piece $T_d$ is a damped natural period of the free vibrations $y_0$ is the displacement of the test piece after zero free vibrations $y_{(0+n)}$ is the displacement of the test piece after zero plus n free vibrations n is a number of free vibrations.

44. The method according to claim 37, further comprising the step of mounting a sensor to the test piece at a displacement measuring point, said sensor being adapted for measuring the time-varying displacement of the test piece, and wherein the test piece is fixed to said frame at a first end of the test piece and at a second end of the test piece opposite the first end;

said displacement measuring point generally coincides with a center of mass of the test piece;

the free vibrations are initiated at a point generally coincidental with said displacement measuring point; and the at least one value of the damping coefficient is calculated according to $$C = \left(\frac{4\pi(M_{sensor} + (0.3610) M_{test})}{T_d}\right) \frac{\ln\left(\frac{y_0}{y_{(0+n)}}\right)}{\sqrt{1 - \left(\frac{\ln\left(\frac{y_0}{y_{(0+n)}}\right)}{2\pi n}\right)^2}}$$

wherein

C is the damping coefficient of the test piece $M_{sensor}$ is a mass of said sensor $M_{test}$ is a mass of the test piece $T_d$ is a damped natural period of the free vibrations $y_0$ is the displacement of the test piece after zero free vibrations $y_{(0+n)}$ is the displacement of the test piece after zero plus n free vibrations n is a number of free vibrations.

45. The method according to claim 38, further comprising the step of mounting a sensor to the test piece at a displacement measuring point, said sensor being adapted for measuring the time-varying displacement of the test piece, and wherein the at least one value of the stiffness coefficient is calculated according to $$K_L = \frac{4\pi^2(kM_{sensor} + k'M_{test})}{T_d^2\left(1 - \left(\frac{\ln\left(\frac{y_0}{y_{(0+n)}}\right)}{2\pi n}\right)^2\right)}$$

wherein
$K_L$ is the stiffness coefficient of the test piece
k is a geometric coefficient corresponding to a position of said displacement measuring point
$M_{sensor}$ is a mass of said sensor
k' is a geometric coefficient corresponding to a position of said at least one fixing point on the test piece
$M_{test}$ is a mass of the test piece
$T_d$ is a damped natural period of the free vibrations
$y_0$ is the displacement of the test piece after zero free vibrations
$y_{(0+n)}$ is the displacement of the test piece after zero plus n free vibrations
n is a number of free vibrations.

46. The method according to claim 38, further comprising the step of mounting a sensor to the test piece at a displacement measuring point, said sensor being adapted for measuring the time-varying displacement of the test piece, and wherein
the test piece is fixed to said frame at a first end of the test piece;
said displacement measuring point is at a second end of the test piece opposite the first end;
the free vibrations are initiated at a point generally coincidental with said displacement measuring point; and
the at least one value of the stiffness coefficient is calculated according to $$K_L = \frac{4\pi^2(M_{sensor} + (0.2357)M_{test})}{T_d^2\left(1 - \left(\frac{\ln\left(\frac{y_0}{y_{(0+n)}}\right)}{2\pi n}\right)^2\right)}$$

wherein
$K_L$ is the stiffness coefficient of the test piece
$M_{sensor}$ is a mass of said sensor
$M_{test}$ is a mass of the test piece
$T_d$ is a damped natural period of the free vibrations
$y_0$ is the displacement of the test piece after zero free vibrations
$y_{(0+n)}$ is the displacement of the test piece after zero plus n free vibrations
n is a number of free vibrations.

47. The method according to claim 38, further comprising the step of mounting a sensor to the test piece at a displacement measuring point, said sensor being adapted for measuring the time-varying displacement of the test piece, and wherein
the test piece is fixed to said frame at a first end of the test piece and at a second end of the test piece opposite the first end;
said displacement measuring point generally coincides with a center of mass of the test piece;
the free vibrations are initiated at a point generally coincidental with said displacement measuring point; and
the at least one value of the stiffness coefficient is calculated according to $$K_L = \frac{4\pi^2(M_{sensor} + (0.3610)M_{test})}{T_d^2\left(1 - \left(\frac{\ln\left(\frac{y_0}{y_{(0+n)}}\right)}{2\pi n}\right)^2\right)}$$

wherein
$K_L$ is the stiffness coefficient of the test piece
$M_{sensor}$ is a mass of said sensor
$M_{test}$ is a mass of the test piece
$T_d$ is a damped natural period of the free vibrations
$y_0$ is the displacement of the test piece after zero free vibrations
$y_{(0+n)}$ is the displacement of the test piece after zero plus n free vibrations
n is a number of free vibrations.

48. The method according to claim 30, wherein said method is non-destructive to the sample.

49. The method according to claim 30, wherein the test piece is generally longitudinal in shape.

50. The method according to claim 30, wherein the test piece has a cross-section of arbitrary geometry.

51. The method according to claim 30, wherein the test piece has a cross-section with a geometry that varies along a length of the test piece.

52. The method according to claim 30, wherein the test piece is comprised of isotropic material.

53. The method according to claim 30, wherein the test piece is comprised of orthotropic material.

54. The method according to claim 31, wherein said plurality of values is calculated from the free vibrations resulting from one initiation of free vibrations in the test piece.

55. The method according to claim 30, wherein a test period beginning at initiation of the free vibrations and ending after calculation of said at least one value for said at least one physical property is not greater than 5 seconds.

56. The method according to claim 31, wherein said plurality of values of said at least one physical property is distributed over a dynamic range of said at least one physical property.

57. The method according to claim 30, further comprising the step of providing feedback based on said at least one value of said at least one physical property, said feedback comprising instructions for adjusting a manufacturing process.

58. A method for controlling a process for manufacturing a product, comprising the steps of:
producing a test piece of the product, the test piece having a stable geometry;
removably fixing the test piece to a frame at at least one fixing point, said frame having a natural vibrational frequency different from a frequency of free vibrations of the test piece;
initiating the free vibrations in the test piece;
measuring a time-varying displacement of the test piece during the free vibrations;
calculating at least one value for at least one physical property of the test piece from the time-varying displacement;
adjusting said process for manufacturing the product based on said at least one value for said at least one physical property.

* * * * *